US007060828B2

(12) United States Patent
Madden et al.

(10) Patent No.: US 7,060,828 B2
(45) Date of Patent: Jun. 13, 2006

(54) LIPOSOMAL CAMPTOTHECINS AND USES THEREOF

(75) Inventors: Thomas D. Madden, Vancouver (CA); Sean C. Semple, Vancouver (CA)

(73) Assignee: Inex Pharmaceuticals Corporation, Burnaby (CA)

( * ) Notice: Subject to any disclaimer, the term of this patent is extended or adjusted under 35 U.S.C. 154(b) by 0 days.

(21) Appl. No.: 09/896,811

(22) Filed: Jun. 29, 2001

(65) Prior Publication Data
US 2002/0119990 A1 Aug. 29, 2002

Related U.S. Application Data

(60) Provisional application No. 60/264,616, filed on Jan. 25, 2001, provisional application No. 60/215,556, filed on Jun. 30, 2000.

(51) Int. Cl.
*C07D 491/00* (2006.01)
*C07D 498/00* (2006.01)
*C07D 513/00* (2006.01)
*C07D 515/00* (2006.01)
*C07D 471/00* (2006.01)

(52) U.S. Cl. ........................... 546/48; 424/450
(58) Field of Classification Search ............... 424/450, 424/457, 94.5, 779, 1.45; 430/250; 514/175, 514/885, 946, 963
See application file for complete search history.

(56) References Cited

U.S. PATENT DOCUMENTS

| 5,023,087 | A | 6/1991 | Yau-Young |
| 5,552,156 | A | 9/1996 | Burke |
| 5,837,282 | A | 11/1998 | Fenske et al. |
| 6,355,268 | B1 * | 3/2002 | Slater et al. ............ 424/450 |

FOREIGN PATENT DOCUMENTS

| WO | WO 95/08986 A1 | 4/1995 |
| WO | WO 98/17256 A1 | 4/1998 |
| WO | WO 99/13816 | * 3/1999 |
| WO | WO 99/13816 A2 | 3/1999 |
| WO | WO 99/51202 A2 | 10/1999 |
| WO | WO 00/23052 A1 | 4/2000 |

OTHER PUBLICATIONS

Burris III, et al., *J. Natl. Cancer Inst.*, 84:1816-1820 (1992).
Clements, et al., *Cancer Chemotherm. Pharmacol.*, 44:411-416 (1999).
Emerson, et al., *Cancer Res.*, 55:603-609 (1995).
Erickson-Miller, et al.., *Cancer Chemother. Pharmacol.*, 39:467-472 (1997).
Grochow, et al., *Drug. Metab. Dispos.*, 20(5):706-713 (1992).
Hardman, et al., *Anticancer Res.*, 19:2269-2274 (1999).
Hsiang, et al., *Cancer Res.*, 48:1722-1726 (1988).
Madden, et al., *Chem. Phys. Lipids*, 53:37-46 (1990).
Madden, et al., "Encapsulation of Topotecan in lipid-based carrier systems. Evaluation of drug stability and plasma elimination in a murine model, and comparison of antitumor efficacy against murine L1210 and B16 tumors," *Proc. of ASCO*, 17:*abstract* 754 (1998).
Mayer, et al., *Biochim. Biophys. Acta*, 1025:143-151 (1990).
McCabe, et al., *Cancer Invest.*, 12(3):308-313 (1994).
O'Leary, et al., *Clin. Cancer Res.*, 5:181-187 (1999).
Ormrod, et al., *Drugs*, 58(3)533-551 (1999).
Tardi, et al., *Cancer Res.*, 60:3389-3393 (2000).
Thompson, *Biochim. Biophys. Acta*, 1400:301-319 (1998).
Wall, et al., *J. Am. Chem. Soc.*, 88:3888-3890 (1966).
Abraham, S.A., K. Edwards, et al. "An evaluation of transmembrane ion gradient-mediated encapsulation of topotecan within liposomes," *J Control Release* 96(3): 449-61, 2004.
Apostolidou, E., G. Garcia-Manero, et al. "Phase I Study of OSI-211, a Novel Liposomal Topoisomerase 1 (Topo 1) Inhibitor, in Patients withs Refractory Leukemia," *Blood*, 2002. Abstract #4575.
Biloti, D. N., A. Santana Maria Helena, et al. "Lipid membrane with low proton permeability," *Biochim Biophy Acta* 1611(1-2): 1-4, 2003.
Bom, D., D. P. Curran, et al. "The novel silatecan 7-tert-butyldimethylsilyl-10-hydroxycamptothecin displays high lipophilicity, improved human blood stability, and potent anticancer activity," *J Med Chem* 43(21): 3970-80, 2000.
Bom, D., D. P. Curran, et al. "the highly lipophilic DNA topoisomerase I inhibitor DB-67 displays elevated lactone levels in human blood and potent anticancer activity," *J Control Release* 74(1-3): 325-33, 2001.
Burke, T. G. and D. Bom, "Camptothecin design and delivery approaches for elevating anti-topoisomerase I activities in vivo," *Ann N Y Acad Sci* 922: 36-45, 2000.
Burke, T. G. and X. Gao "Stabilization of topotecan in low pH liposomes composed of distearoylphosphatidylcholine," *J Pharm Sci* 83(7): 967-9, Jul. 1994.

(Continued)

*Primary Examiner*—Christopher S. F. Low
*Assistant Examiner*—Amy Lewis
(74) *Attorney, Agent, or Firm*—Seed Intellectual Property Law Group PLLC

(57) ABSTRACT

This invention relates to improved liposomal camptothecin compositions and methods of manufacturing and using such compositions for treating neoplasia and for inhibiting angiogenesis.

10 Claims, 9 Drawing Sheets

OTHER PUBLICATIONS

Burke, T. G., E. Staubus Alfred, et al. "Liposomal stabilization of Camptothecin lactone ring." *J Am Chem Soc 114*:8318-8319, 1992.

Burke, T. G., Z. Mi, et al. "Liposomal stabilization of camptothecins," *Proc Amer Assoc Cancer Res*. 35:416, Mar. 1994. Abstract #2479.

Chou, T.-H., S.-C. Chen, et al. "Effect of composition on the stability of liposomal irinotecan prepared by a pH gradient method." *Journal of Bioscience and Bioengineering.* 95(4):405-408, 2003.

Chow, D. S. L., G. Chen, et al. "Liposomal camptothecin and 9-nitro-camptothecin: Formulation, pharmacokinetics and preclinical anti-tumor activity." *Proceedings of the Controlled Release Society*, pp. 919-920, 1997.

Chow, D. S., L. Gong, et al. "Modified lactone/carboxylate salt equilibria in vivo by liposomal delivery of 9-nitro-camptothecin." *Ann N Y Acad Sci 922*:164-74, 2000.

Clements, M. K., C. B. Jones, et al. "Antiangiogenic potential of camptothecin and topotecan," *Cancer Chemother Pharmacol 44*(5): 411-6, 1999.

Clements, M. K., S. Wasi, et al. "Camptothecin exhibits selective cytotoxicity towards human breast carcinoma as compared to normal bovine endothelial cells in vitro." *Anticancer Drugs 7*(8): 851-7, 1996.

Colbern, G. T., D. J. Dykes, et al. "Encapsulation of the topoisomerase I inhibitor GL147211C in pegylated (STEALTH) liposomes: pharmacokinetics and antitumor activity in HT29 colon tumor xenografts." *Clin Cancer Res 4*(12): 3077-82, Dec. 1998.

Daoud, S. S., M. I. Fetouh, et al. "Antitumor effect of liposome-incorporated camptothecin in human malignant xenografts." *Anticancer Drugs 6*(1): 83-93, 1995.

Dunton, C. J. "New options for the treatment of advanced ovarian cancer," *Semin Oncol 24(1 Suppl 5)*:S5-2-S5-11, Feb. 1997.

El-Kareh, A. W. and T. W. Secomb "Theoretical models for drug delivery to solid tumors." *Crit Rev Biomed Eng 25*(6): 503-571, 1997.

Emerson, D. L. "Liposomal delivery of camptothecins," *Pharmaceutical Science and Technology Today 3*(6): 205-209, Jun. 2000.

Emerson, D. L., N. Amirgahari, et al. "NX-211, a liposomal formulation of lurtotecan demonstrates enhanced pharmacokinetic and antitumor activity." *Proc Amer Assoc Cancer Res*. 39: 278, Mar. 1998, Abstract #1897.

Emerson, D. L., R. Bendele, et al. "Antitumor efficacy, pharmacokinetics, and biodistribution of NX 211: a low-clearance liposomal formulation of lurtotecan," *Clin Cancer Res 6*(7): 2903-12, Jul 2000.

Emerson, D., A. Gray, et al. "The topoisomerase I inhibitor, NX211 demonstrates significant in vivo activity against human acute myeloid leukemia (AML) engrafted in SCID mice." *Blood*, 1999. Abstract #4223.

Erickson-Miller, C. L., R. D. May, et al. "Differential toxicity of camptothecin, topotecan and 9-aminocamptothecin to human, canine, and murine myeloid progenitors (CFU-GM) in vitro." *Cancer Chemother Pharmacol 39*(5): 467-72, 1997.

Garcia-Carbonero, R. and J.G. Supko "Current perspectives on the clinical experience, pharmacology, and continued development of the camptothecins." *Clin Cancer Res 8*(3): 641-661, Mar. 2002.

Gelmon, K., H. Hirte, et al. "A phase 1 study of OSI-211 given as an intravenous infusion days 1, 2, and 3 every three weeks in patients with solid cancers." *Invest New Drugs 22*93): 263-75, 2004.

Giles, F. J., M. S. Tallman, et al. "Phase I and pharmacokinetic study of a low-clearance, unilamellar liposomal formulation of lurtotecan, a topoisomerase 1 inhibitor, in patients with advanced leukemia." *Cancer 100*(7): 1449-58, Apr. 2004.

Giles, F., M. Tallman, et al. "Phase I and pharmacokinetic study of OSI-211, a liposomal formulation of lurtotecan, a topoisomerase 1 inhibitor, in patients with advanced leukemia." *Blood*, p. 2516, 2003. Abstract #4732.

Guo, W., A. Ahmad, et al. "Determination by liquid chromatography with fluorescence detection of total 7-ethyl-10-hydroxy-camptothecin (SN-38) in beagle dog plasma after intravenous administration of liposome-based SN-38 (LE-SN38)." *J Chromatogr B 791*(1-2): 85-92, 2003.

Hatefi, A. and B. Amsden "Camptothecin delivery methods." *Pharm Res 19*(10):1389-1399, Oct. 2002.

Khan, S., A. Ahmad, et al. "A sensitive and rapid liquid chromatography tandem mass spectrometry method for quantitative determination of 7-ethyl-10-hydroxycamptothecin (SN-38) in human plasma containing liposome-based SN-38 (LE-SN38)." *Biomedical chromatography—BMC 17*(8): 493-9, 2003.

Knight, V., E. S. Kleinerman, et al. "9-Nitrocamptothecin liposome aerosol treatment of human cancer subcutaneous xenografts and pulmonary cancer metastases in mice." *Ann N Y Acad Sci 922*: 151-63, 2000.

Knight, V., N. Koshkina, et al. "Anti-cancer activity of 9-nitrocamptothecin liposome aerosol in mice." *Trans Am Clin Climatol Assoc 111*: 135-45, 2000.

Knight, V., N. V. Koshkina, et al. "Anticancer effect of 9-nitrocamptothecin liposome aerosol on human cancer xenografts in nude mice." *Cancer Chemother Pharmacol 44*(3): 177-86, 1999.

Koshkina, N. V., B. E. Gilbert, et al. "Distribution of camptothecin after delivery as a liposome aerosol or following intramuscular injection in mice." *Cancer Chemother Pharmacol 44*(3): 187-92, 1999.

Koshkina, N. V., E. S. Kleinerman, et al. "9-Nitrocamptothecin liposome aerosol treatment of melanoma and osteosarcoma lung metastases in mice." *Clin Cancer Res 6*(7): 2876-80, 2000.

Koshkina, N. V., V. Knight, et al. "Improved respiratory delivery of the anticancer drugs, camptothecin and paclitaxel, with 5% CO2-enriched air: pharmacokinetic studies." *Cancer Chemother Pharmacol 47*(5): 451-6, 2001.

Lei, S., P.-Y. Chien, et al. "Enhanced therapeutic efficacy of a novel liposome-based formulation of SN-38 against human tumor models in SCID mice." *Anticancer Drugs 15*(8):773-8, 2004.

Liu, J. J., R. L. Hong, et al. "Simple and efficient liposomal encapsulation of topotecan by ammonium sulfate gradient: stability, pharmacokinetic and therapeutic evaluation." *Anticancer Drugs 13*(7): 709-17, 2002.

Liu, X., B. C. Lynn, et al. "A versatile prodrug approach for liposomal core-loading of water-insoluble camptothecin anticancer drugs." *J Am Chem Soc 124*(26): 7650-1, 2002.

Loos, W. J., D. Kehrer, et al. "Liposomal lurtotecan (NX211): determination of total drug levels in human plasma and urine by reversed-phase high performance liquid chromatography." *J Chromatogr B 738*(1): 155-63, 2000.

Loos, W. J., J. Verweij, et al. "Structural identification and biological activity of 7-methyl-10, 11-ethylenedioxy-20(S)-camptothecin, a photodegradant of lurtotecan." *Clin Cancer Res* 8(3): 856-62, Mar. 2002.

Lundberg, B. B. "Biologically active camptothecin derivatives for incorporation into liposome bilayers and lipid emulsions." *Anticancer Drug Des* 13(5): 453-61, 1998.

Luo, J. D., Z. Q. Ma, et al. "[Studies on polyphase liposome of camptothecin, PL-CSA]." *Yao xue xue bao = Acta pharmaceutica Sinica* 19(1): 63-8, 1984.

Lynam, E., D. J. Landfair, et al. "Camptothecin analogue efficacy in vitro: Effect of liposomal encapsulation of GI147211C (NX211)." *Drug Delivery: Journal of Delivery and Targeting of Therapeutic Agents* 6:51-62, 1999.

MacKenzie, M. J., H. W. Hirte, et al. "A phase I study of OSI-211 and cisplatin as intravenous infusions given on day 1, 2 and 3 every 3 weeks in patients with solid cancers." *Ann Oncol* 15(4): 665-70, 2004.

Maliepaard, M., M. A. Van Gastelen, et al. "Circumvention of breast cancer resistance protein (BCRP)-mediated resistance to camptothecins in vitro using non-substrate drugs or the BCRP inhibitor GF120918." *Clin Cancer Res* 7(4): 935-941, Apr. 2001.

Meerum, T. J. M., J. H. M. Schellens, et al. "Clinical pharmacology of anticancer agents in relation to formulations and administration routes." *Cancer Treat Rev* 25(2): 83-101, 1999.

Messerer, C. L., E. C. Ramsay, et al. "Liposomal irinotecan: formulation development and therapeutic assessment in murine xenograft models of colorectal cancer." *Clin Cancer Res* 10(19): 6638-49, Oct. 2004.

Mi, Z. and T. G. Burke "Differential interactions of camptothecin lactone and carboxylate forms with human blood components." *biochemistry* 33(34): 10325-36, 1994.

Proulx, M.E., A. Desormeaux, et al. "Treatment of visceral leishmaniasis with sterically stabilized liposomes containing camptothecin." *Antimicrob Agents Chemother* 45(9): 2623-7, 2001.

Proulx, M. E., J.F. Marquis, et al. "Incorporation of camptothecin into liposomes: A new approach for the treatment of leishmaniasis." *Abstracts of the 39th Annual Interscience Conference on Antimicrobial Agents and Chemotherapy*, San Francisco, 1999. Abstract 1856.

Sadzuka, Y. "Effective prodrug liposome and conversion to active metabolite." *Curr Drug Metab* I(1): 31-48, 2000.

Sadzuka, Y., S. Hirotsu, et al. "The study of polyethyleneglycol-coated liposomes containing CPT-11." *J Liposome Res*.7(2&3): 241-260, 1997.

Sadzuka, Y., S. Hirotsu, et al. "Effect of liposomalization on the antitumor activity, side-effects and tissue distribution of CPT-11." *Cancer Lett* 127(1-2): 99-106, 1998.

Sadzuka, Y., S. Hirotsu, et al. "Effective irinotecan (CPT-11)-containing liposomes: intraliposomal conversion to the active metabolite SN-38." *Jpn J Cancer Res* 90(2): 226-32, Feb. 1999.

Seiden, M. V., F. Muggia, et al. "A phase II study of liposomal lurtotecan (OSI-211) in patients with topotecan resistant ovarian cancer." *Gynecol Oncol* 93(1): 229-32, 2004.

Stano, P., S. Bufali, et al. "Novel camptothecin analogue (gimatecan)-containing liposomes prepared by the ethanol injection method." *J Liposome Res* 14(1-2): 87-109, 2004.

Subramanian, D. and M. T. Muller "Liposomal encapsulation increases the activity of the topoisomerase I inhibitor topotecan." *Oncol Res* 7(9): 461-9, 1995.

Tardi, P., E. Choice, et al. "Liposomal encapsulation of topotecan enhances anticancer efficacy in murine and human xenograft models." *Cancer Res* 60(13): 3389-93, Jul. 2000.

Tomkinson, B. E., E. Brown, et al. "In vivo evaluation of NX 211 in combination with cisplatin, 5-FU, and paclitaxel." *Proc Amer Assoc Cancer Res*. 41:144, Mar. 2000.

Tomkinson, B., R. Bendele, et al. "OSI-211, a novel liposomal topoisomerase I inhibitor, is active in SCID mouse models of human AML and ALL." *Leukemia Research* 27(11): 1039-50, 2003.

Verschraegen, C. F., B. E. Gilbert, et al. "Feasibility, phase I, and pharmacological study of aerosolized liposomal 9-nitro-20(S)-camptothecin in patients with advanced malignancies in the lungs." *Ann N Y Acad Sci* 922: 352-4, 2000.

Verschraegen, C. F., B. E. Gilbert, et al. "Clinical evaluation of the delivery and safety of aerosolized liposomal 9-nitro-20(s)-camptothecin in patients with advanced pulmonary malignancies." *Clin Cancer Res* 10(7): 2319-26, Apr. 2004.

Verschraegen, C. F., K. Jaeckle, et al. "Alternative administration of camptothecin analogues." Ann N Y Acad Sci 922: 237-46, 2000. Abstract only.

Zhang, J. A., T. Xuan, et al. "Development and characterization of a novel liposome-based formulation of SN-38." *Int J Pharm* 271(1-2): 93-107, 2004.

Zhang, Q. M., X. Q. Gu, et al. "[A method for determining the encapsulation ratio of camptothecin in polyphase liposome and studies on its leakage property]" *Yao xue xue bao = Acta Pharmaceutica Sinica* 22(12): 918-22, 1987.

Zufia, L., A. Aldaz, et al. "Separation methods for camptothecin and related compounds." *J Chromatogr B* 764(1-2): 141-159, 2001.

Zunino, F., S. Dallavalle, et al. "Current status and perspectives in the development of camptothecins." *Curr Pharm Des* 8(27): 2505-2520, 2002.

Desjardins, J. P., E. A. Abbott, et al. (2001). "Biodistribution of NX211, liposomal lurtotecan, in tumor-bearing mice." *Anticancer Drugs* 12(3): 235-45, Mar. 2001.

Begu, S., C. Tourne-Peteilh, et al. "Spectrofluorimetry study of interaction of camptothecin with liposomal bilayer." *Luminescence* 15:78-79, 2000.

Bell, C. B., D. J. Landfair, et al. "Topoisomerase I (TOPO-1) modulation by liposomal GI147211 (NX211)." *Proc Amer Assoc Cancer Res* 41, p. 773, Mar. 2000. Abstract #4915.

Bevins, R. L., D. Bom, et al. "Tumor cell cycle disruption and apoptosis induced by DB-67, a highly lipophilic camptothecin displaying improved human blood stability." *Proc Amer Assoc Cancer Res* 42, p. 102, Mar. 2001. Abstract #554.

Bom, D. C., J. Zhang, et al. "The structural basis of camptothecin loading and retention in liposomal drug carriers." *Proc Amer Assoc Cancer Res* 42:374, Mar. 2001. Abstract #2016.

Burke, T. G., A. J. Chavan, et al. "Development and evaluation of a liposomal formulation of highly lipophilic 7-t-butyldimethylsilyl-10-hydroxy-camptothecin." *Proc Amer Assoc Cancer Res* 40, Mar. 1999. Abstract #752.

Burke, T. G., D. Subramanian, et al. "Enhanced bloodstream stability and in vivo activity of topotecan formulated in liposomes." *Pharm Res* 11(10):S-323, Oct. 1994. Abstract # PDD 7596.

Burke, T. G., S. Gao Xian, et al. "Liposomal stabilization of the lactone ring of camptothecin anticancer drugs." *Pharm Res* 10(10):S-220, Oct. 1993. Abstract # PDD 7483.

Burke, T. G., X. Liu, et al. "A versatile pro-drug approach for the liposomal core loading of camptothecin anticancer drugs." *Proc Amer Assoc Cancer Res 43*, Mar. 2002. Abstract #5731.

Burke, T. G., Z. Mi, et al. (1994). "Liposomal formulations of camptothecins for cancer treatment." Abstracts of Papers American Chemical Society, In *Proceedings of the 208th ACS National Meeting*, Washington, DC, Aug. 21-25, 1994. Abstract #50.

Cao, Z. and C. Giovanella Beppino, "Liposomal prodrugs comprising derivatives of camptothecin and methods of treating cancer these prodrugs." *Official Gazette of the United States Patent and Trademark Office Patents 1256*(1):372, Mar. 2002. US Patent 6,352,996 B1.

Chavan, A. J., K. A. Fraley, et al. "A comparative study of the human blood stability characteristics of remote-loaded liposomal carriers containing clinically-relevant camptothecins." *Proc Amer Assoc Cancer Res 40*:417, Mar. 1999. Abstract #6019.

Chen, G., A. Double John, et al. "Characterization of liposomal mimetic formulations for selective targeting." *Pharm Res 13*S-161, Sep. 1996. Abstract # PPDM 8345.

Chen, G., W. Barry Brian, et al. "Pharmacokinetic evaluation of liposomal camptothecin." *Pharm Res 13*(9):S-479, Sep. 1996.

Cherian, M. "Lyophilizate of lipid complex of water insoluble camptothecins." *Official Gazette of the United States Patent and Trademark Office Patents 1269*(3), Apr. 2003. U.S. Patent 6,548,071 B1.

Chien, P.-Y., S. Sheikh, et al. "Cytotoxicity evaluation of a liposome-based formulation of SN38 in human and murine cancer cell lines." *Proc Amer Assoc Cancer Res 44*:314, Jul. 2003. Abstract #1607.

Choice, E., M. B. Bally, et al. "Delivery of topotecan using liposomes: Drug loading into liposomes and drug and carrier pharmacokinetics in female Balb/c mice." *Proc Amer Assoc Cancer Res 40*, Mar. 1999. Abstract #753.

Chow, D. S. L., G. Chen, et al. "Pharmacokinetics and in vivo antitumor activity of liposomal encapsulated camptothecin and its analog." *Proc Amer Assoc Cancer Res 38*, Mar. 1997.

Cortesi, R., E. Esposito, et al. "Formulation study for the antitumor drug camptothecin: Liposomes, micellar solutions and a microemulsion." *Int J Pharm 159*:95-103, 1997.

Cortesi, R., E. Esposito, et al. "Liposomes, micelles and microemulsions as new delivery systems for camptothecin." *Eur J Pharm Sci 6*(Supp. 1):S3, 1998. Abstract #12.

Dallavalle, S., L. Merlini, et al. "Perspectives in camptothecin development." *Expert Opinion on Therapeutic Patents 12*(6):837-844, 2002.

Daoud, S. S., M. I. Fetouh, et al. (1993). "Multilamellar liposomes as a delivery system for camptothecin (NSC 94600) and 9-aminocamptothecin (NSC 603071)." in *Proc Amer Assoc Cancer Res*. Orlando, FL, May 19-22, 1993, 367. Abstract #2188.

Desjardins, J. P., D. L. Emerson, et al. "Biodistribution of NX 211, liposomal GI147211, in tumor bearing mice." *Proc Amer Assoc Cancer Res 41*702, Mar. 2000. Abstract #4467.

Emerson, D. L., N. Amirghahari, et al. "Enhanced in vivo antitumor efficacy of the liposome formulated topoisomerase I inhibitor Lurtotecan." *Proc Amer Assoc Cancer Res 40*:113,Mar. 1999. Abstract #751.

Emerson, D. L., R. Bendele, et al. "In vivo antitumor efficacy of liposomal lurtotecan (NX 211) in human xenografts." *Proc Amer Assoc Cancer Res 42*:100, Mar. 2001. Abstract #545.

Gelmon, K. A., E. Eisenhauer, et al. "Phase 1 study of NX 211 (liposomal lurtotecan) given as an intravenous infusion on days 1, 2, and 3 every weeks in patients (pts) with solid tumors- An NCIC clinical trials group study." *Proc Amer Assoc Cancer Res 41*:610, Mar. 2000. Abstract #3879.

Gilbert, B. E., A. Seryshev, et al. "9-nitrocamptothecin liposome aerosol: lack of subacute toxicity in dogs." *Inhal Toxicol 14*(2): 185-97, 2002.

Gong, L., B. C. Giovanella, et al. "Improved lactone stability of 9-nitro-camptothecin in vitro and in vivo by liposomal formulation." *Proc Amer Assoc Cancer Res 39*:430, Mar. 1998. Abstract #2926.

Gong, L., B. C. Giovanella, et al. "Sustained organ exposure to 9-nitro-camptothecin (9NC) lactone form by liposomal delivery." *Proc Amer Assoc Cancer Res 40*:417, Mar. 1999. Abstract #2756.

Gong, L., G. Chen, et al. "Development and characterization of liposomal formulation of 9-nitro-camptothecin." *Pharm Res 13*:S-162, Sep. 1996. Abstract #6021.

Haas, H., B. Schulze, et al. "Strong antitumor efficacy of a cationic liposomal camptothecin formulation (LipoCamTM) in the subcutaneous human melanoma A-375 in nude mice." *Proc Amer Assoc Cancer Res 44*:350-351, Jul. 2003. Abstract # R1793.

Kamath, N., K. Sarkar Asis, et al. "Therapeutic efficacy of liposome-based formulation of SN38 against leukemia model in CD2F1 mice." *Proc Amer Assoc Cancer Res 44*, 2nd Ed., Jul. 2003. Abstract #1784.

Khan, S., S. Ali, et al. "Liposome based formulation of SN-38 (LE-SN38): A four-cycle toxicity evaluation in beagle dogs." *Toxicological Sciences 72*(S-1), Mar. 2003. Abstract #1873.

Knight, J. V., B. Gilbert, et al. "Small particle liposome aerosols for delivery of anti-cancer drugs." *Official Gazette of the United States Patent and Trademark Office Patents 1236*(3):2973, Jul 18, 2000. U.S. Patent 6,090,407.

Koshkina, N. V., B. E. Gilbert, et al. (1999). "Pharmacokinetics and tissue distribution of camptothecin after delivery as a liposome aerosol or following intramuscular injection in mice." *Proc Amer Assoc Cancer Res 40*:10, Mar. 1999. Abstract #734.

Kruszewski, S., A. S. Chavan, et al. (2000). "Comparison of the human blood chemistry of free versus liposomal forms of the clinically-relevant topoisomerase I inhibitor Lurtotecan (GI147221)." *Proc Amer Assoc Cancer Res 41*:324, Mar. 2000. Abstract #2056.

Lerchen, H. G. "Camptothecin antitumor agents." *Idrugs 2*(9):896-906, 1999.

Loos, W. J., D. F. S. Kehrer, et al. "Clinical pharmacodynamics of liposomal lurtotecan (NX211): Urinary excretion predicts hematologic toxicity." *Proc Amer Assoc Cancer Res 42*:102, Mar. 2001. Abstract #551.

Lopez-Barcons, L. A., J. Zhang, et al. "The novel highly lipophilic topoisomerase I inhibitor DB67 is effective in the treatment of liver metastases of murine CT-26 colorectal carcinoma." *Proc Amer Assoc Cancer Res 44*(2): 348, 2003. Abstract #1782.

Lynam, E., D. J. Landfair, et al. "Camptothecin analogue efficacy in vitro: Effect of liposomal encapsulated of Ci147211C (Lurtotecan) in vitro cytotoxicity for multiple tumor cell types." *Proc Amer Assoc Cancer Res 31*:421, Mar. 1998.

Mamot, C., D. C. Drummond, et al. "Liposome-based approaches to overcome anticancer drug resistance." *Drug Resistance Updates 6*:271-279, 2003.

Michaelis, U., B. Schulze, et al. "Cationic liposomes (Catioms) to target tumor neovasculature." Abstracts of Papers American Chemical Society, in *Proceedings of the 226th ASC National Meeting*, New York, Sep. 7-11, 2003.

Moynihan Karen, L., L. Emerson David, et al. "Liposomal camptothecin formulations." *Official Gazette of the United States Patent and Trademark Office Patents*, 2004. U.S. Patent 6,740,335B1.

Pal, A., S. Sheikh, et al. "Enhanced antitumor efficacy of liposome-based formulation of SN38 against human pancreatic tumor in SCID mice." *Proc Amer Assoc Cancer Res*, 2003. Abstract #1785.

Poirot, K., Y. Zou, et al. "Liposomal-camptothecin composed of cationic phospholipids containing unsaturated fatty acids: Formulation and cytotoxicity studies." *Proc Amer Assoc Cancer Res 37*:300, Mar. 1996. Abstract #2039.

Sadzuka, Y., S. Hirotsu, et al. "Antitumor effect of CPT-11 encapsulated liposome and conversion to active metabolite." *J Liposome Res*, pp. 101-102, 1998.

Sarkar, A., N. Kamath, et al. "Toxicity evaluation of a liposome-based formulation of SN38 in mice." *Toxicol Sci 72*(S-1):83, Mar. 2003. Abstract #403.

Semple, S. C., B. L. S. Mui, et al. "Comparative efficacy and therapeutic index to topotecan and liposomal topotecan in murine and human solid tumor models." *Pro Amer Assoc Cancer Res 44*, Jul. 2003. Abstract #3658.

Semple, S. C., S. K. Klimuk, et al. "Pre-clinical evaluation of liposomal topotecan: increased efficacy and therapeutic index in murine and human xenograft tumor models compared to free drug." *Proc Amer Assoc Cancer Res 42*:374, Mar. 2001. Abstract #2015.

Sugarman, S. and R. Perez-Soler "Liposomal camptothecin: Formulation and cytotoxicity against KB cells." *Proc Amer Assoc Cancer Res*, Orlando, FL, May 19-22, 1993, p. 422. Abstract #2519.

Tanyeli, C., D. Bom, et al. "Formulation and pharmacological characterization of the novel polyamine camptothecin CT-17 encapsulated in low-clearance liposomes." *Proc Amer Assoc Cancer Res 42*:255, Mar 2001. Abstract #1379.

Tomkinson, B., E. Brown, et al. (2001). "Efficacy of NX 211 in SCID mouse models of human leukemia." *Proc Amer Assoc Cancer Res 42*:100, 2001. Abstract #542.

Ulukan, H., D. Roy, et al. "Controlled release of topotecan from thermosensitive liposomes." *Proc Amer Assoc Cancer Res 36*:308, Mar. 1995. Abstract #1833.

Yu, N. Y., C. Conway, et al. "STEALTH liposome formulation enhances antitumor efficacy of CKD-602, a topoisomerase I inhibitor, in human tumor xenograft models." *Proc Amer Assoc Cancer Res 45*: 710, Mar. 2004. Abstract #3069.

Zunino, F. and G. Pratesi "Camptothecins in clinical development." *Expert Opin Investig Drugs 13*(3): 269-284, 2004.

Madden T. et al., "Encapsulation of Topotecan in Lipid-Based Carrier Systems: Evaluation of Drug Stability and Plasma Elimination in a Murine Model, and Comparison of Antitumor Efficacy Against Murine L1210 and B16", *Proceedings from 34th Annual ASCO Meeting*, 1998. Abstract #754.

\* cited by examiner

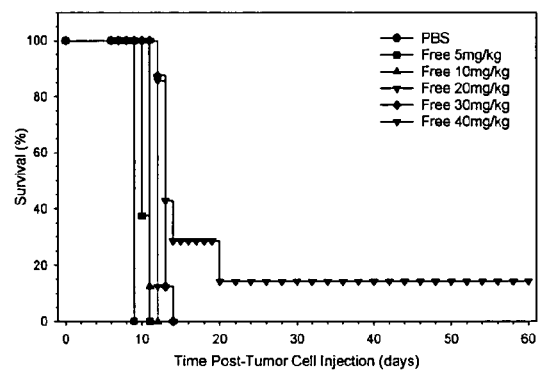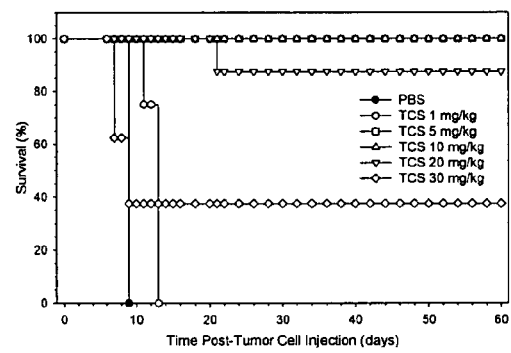
FIG. 3

LIPOSOMAL CAMPTOTHECINS AND USES THEREOF

CROSS REFERENCE TO RELATED APPLICATIONS

The present application claims priority to U.S. Provisional Patent Application Nos. 60/215,556, filed Jun. 30, 2000, and 60/264,616, filed Jan. 26, 2001, both of which are hereby incorporated by reference in their entireties for all purposes. U.S. patent application No. 09/896,812, filed Jun. 29, 2001, entitled "Liposomal Antineoplastic Drugs and Uses Thereof," is hereby incorporated by reference for all purposes.

BACKGROUND OF THE INVENTION

This invention relates to improved liposomal camptothecin compositions and methods of manufacturing and using such compositions for treating neoplasia and for inhibiting angiogenesis.

Therapeutic camptothecins, such as Topotecan (9-dimethylaminomethyl-10-hydroxy-camptothecin; Hycamtin™), and Irinotecan, are a semi-synthetic, water soluble derivative of camptothecin, an alkaloid extracted from the stem wood of the Chinese tree Camptotheca acuminata (Wall, et al., *J. Am. Chem. Soc.* 88:3888–3890 (1966)). Camptothecins belong to the topoisomerase inhibitor class of antineoplastic agents, specifically inhibiting the action of the nuclear enzyme topoisomerase I which is involved in DNA replication (Hsiang, et al., *Cancer Res.* 48:1722–1726 (1988)). As such, topotecan exhibits a cell cycle-specific mechanism of action, acting during S-phase (DNA replication) to cause irreversible double strand breaks in DNA that ultimately lead to G2 cell cycle arrest and apoptosis. In the free form, the drug has a broad spectrum of activity against a range of tumor cell lines and murine allograft and human xenograft tumor models (McCabe, F. L. et al, *Cancer Invest* 12:308–313 (1994); Emerson, et al, *Cancer Res.* 55:603–609 (1995); Thompson, *Biochim. Biophys. Acta* 1400:301–319 (1998); Ormrod, et al., *Drugs* 58:533–551 (1999); Hardman, et al., *Anticancer Res.* 19:2269–2274 (1999)). More recently, evidence has emerged that topotecan has strong anti-angiogenic properties that may contribute to its anti-tumor mechanism of action (O'Leary, et al., *Clin. Cancer Res.* 5:181–187 (1999); Clements, et al., *Cancer Chemother. Pharmacol.* 44:411–416 (1999)). All these treatments are associated with dose-limiting toxicity such as non-cumulative myelosuppression leading to anaemia, neutropenia and thrombocytopenia, and gastrointestinal-related toxicity, including mucositis and diarrhea. Clinically, topotecan has been approved for second-line therapy in ovarian and small cell lung cancer (SCLC) and is currently the focus of extensive clinical evaluation.

Lipid formulations of camptothecins have been proposed as therapeutic agents (see, U.S. Pat. No. 5,552,156 and PCT Publication No. WO 95/08986. However, not all lipid formulations are equal for drug delivery purposes and extensive research continues into formulations which demonstrate preferred characteristics for drug loading and storage, drug administration, pharmacokinetics, biodistribution, leakage rates, tumor accumulation, toxicity profile, and the like. With camptothecins, the field is further complicated because dose limiting toxicities in humans may be 10-fold lower than in mice (Erickson-Miller, et al., *Cancer Chemother. Pharmacol.* 39:467–472 (1997)).

In short, camptothecins are a promising class of antineoplastic agents, and lipid formulations of these drugs could prove very useful. However, to date, lipid formulations have not provided sufficiently remarkable activity to warrant clinical advancement. It is an object of the instant invention to provide novel lipid formulated camptothecins having novel clinical utility.

SUMMARY OF THE INVENTION

The present invention provides improved liposomal camptothecin (e.g., topotecan) compositions having surprisingly increased clinical efficacy and decreased collateral toxicity. In addition, the present invention provides methods of using such liposomal camptothecin compositions to treat neoplasia and to inhibit angiogenesis.

In one aspect, the present invention provides a liposomal camptothecin unit dosage form comprising a camptothecin dosage of from about 0.015 mg/$M^2$/dose to about 1 mg/$M^2$/dose and a lipid, wherein the liposomal camptothecin unit dosage form has a drug:lipid ratio (by weight) of about 0.005 to about 0.01. In a preferred embodiment, the unit dosage form comprises a camptothecin dosage of from about 0.15 mg/$M^2$/dose to about 0.5 mg/$M^2$/dose.

In one embodiment, the present invention provides a liposomal topotecan unit dosage form is about 0.01 mg/$M^2$/dose to about mg/$M^2$/dose and a lipid and having a drug:lipid ratio (by weight) of about 0.05 to about 0.2. In certain aspects, the drug:lipid ratio (by weight) is about 0.05 to about 0.15. In another aspect, the liposomal topotecan unit dosage form is about 1 mg/$M^2$/dose to about 4 mg/$M^2$/dose of topotecan.

It will be readily apparent to those of skill in the art that any of the camptothecins can be formulated in accordance with the present invention. In a preferred embodiment, the present invention provides liposomal topotecan unit dosage forms. In addition, it will be readily apparent to those of skill in the art that any of a variety of lipids can be used to form the liposomal compositions of the present invention. In a presently preferred embodiment, the lipid comprises a mixture of sphingomyelin and cholesterol, preferably at a sphingomyelin:cholesterol molar ratio of about 70:30 to about 40:45.

In another aspect, the present invention provides a liposomal camptothecin (e.g., topotecan) formulation, wherein the formulation retains greater than 50% of the camptothecin as the active lactone species after 12 hours in blood circulation. In a preferred embodiment, the formulation retains greater than 80% of the camptothecin as the active lactone species after 12 hours in blood circulation. In another aspect, the present invention provides a lipid formulation of a camptothecin (e.g., topotecan), comprising a camptothecin, sphingomyelin, cholesterol and a divalent ionophore, such as a divalent cation ionophore. In a preferred embodiment, the divalent ionophore is present in trace amounts. In another preferred embodiment, the ionophore is present in greater than trace amounts.

In still another aspect, the present invention provides a method of treating a solid tumor in a human afflicted therewith, the method comprising administering to the human an effective amount of a liposomal camptothecin unit dosage form in a pharmaceutically acceptable carrier. It will be readily apparent to those of skill in the art that any of a variety of solid tumors can be treated using the compositions of the present invention. In a preferred embodiment, the solid tumor to be treated is selected from the group consisting of solid tumors of the lung, mammary, colon and prostate. In another preferred embodiment, the method further comprises co-administration of a treatment or active agent suitable for treating neutropenia or platelet deficiency. In a preferred embodiment, the camptothecin dosage in the liposomal camptothecin unit dosage form ranges from 0.015 mg/M$^2$/dose to about 1 mg/M$^2$/dose. In another preferred embodiment, the liposomal camptothecin unit dosage form has a drug:lipid ratio (by weight) of about 0.005 to about 0.01. In a preferred embodiment, the unit dosage form comprises a camptothecin dosage of from about 0.15 mg/M$^2$/dose to about 0.5 mg/M$^2$/dose. Again, it will be readily apparent to those of skill in the art that any of the camptothecins can be formulated in accordance with the present invention. In a preferred embodiment, a liposomal topotecan unit dosage form is used to treat the solid tumors. In addition, it will be readily apparent to those of skill in the art that any of a variety of lipids can be used to form the liposomal compositions of the present invention. In a presently preferred embodiment, the liposomal unit dosage form comprises a mixture of sphingomyelin and cholesterol, preferably at a spingomyelin:cholesterol ratio (by weight) of about 30:70 to about 60:40.

Other features, objects and advantages of the invention and its preferred embodiments will become apparent from the detailed description which follows.

BRIEF DESCRIPTION OF THE DRAWINGS

FIG. 3. Efficacy of free (A) and encapsulated (B) topotecan in an intravenous L1210 murine leukemia model-single dose. L1210 cells (10$^5$ cells in 200 μl) were injected i.v. into the tail vein of BDF-1 mice on day 0. Topotecan was encapsulated in SM:CH (55:45) vesicles at a drug-to-lipid ratio of 0.10 (w/w) using the Mg-A23187 method as described in Experimental. All dilutions were made in sterile 0.9% saline immediately prior to injection. Drug administration was made via the lateral tail vein at 1 day post-tumor cell injection. Each group consisted of 8 animals. Data is from NCTEF-005.

DETAILED DESCRIPTION OF THE INVENTION AND PREFERRED EMBODIMENTS

Figure 1:
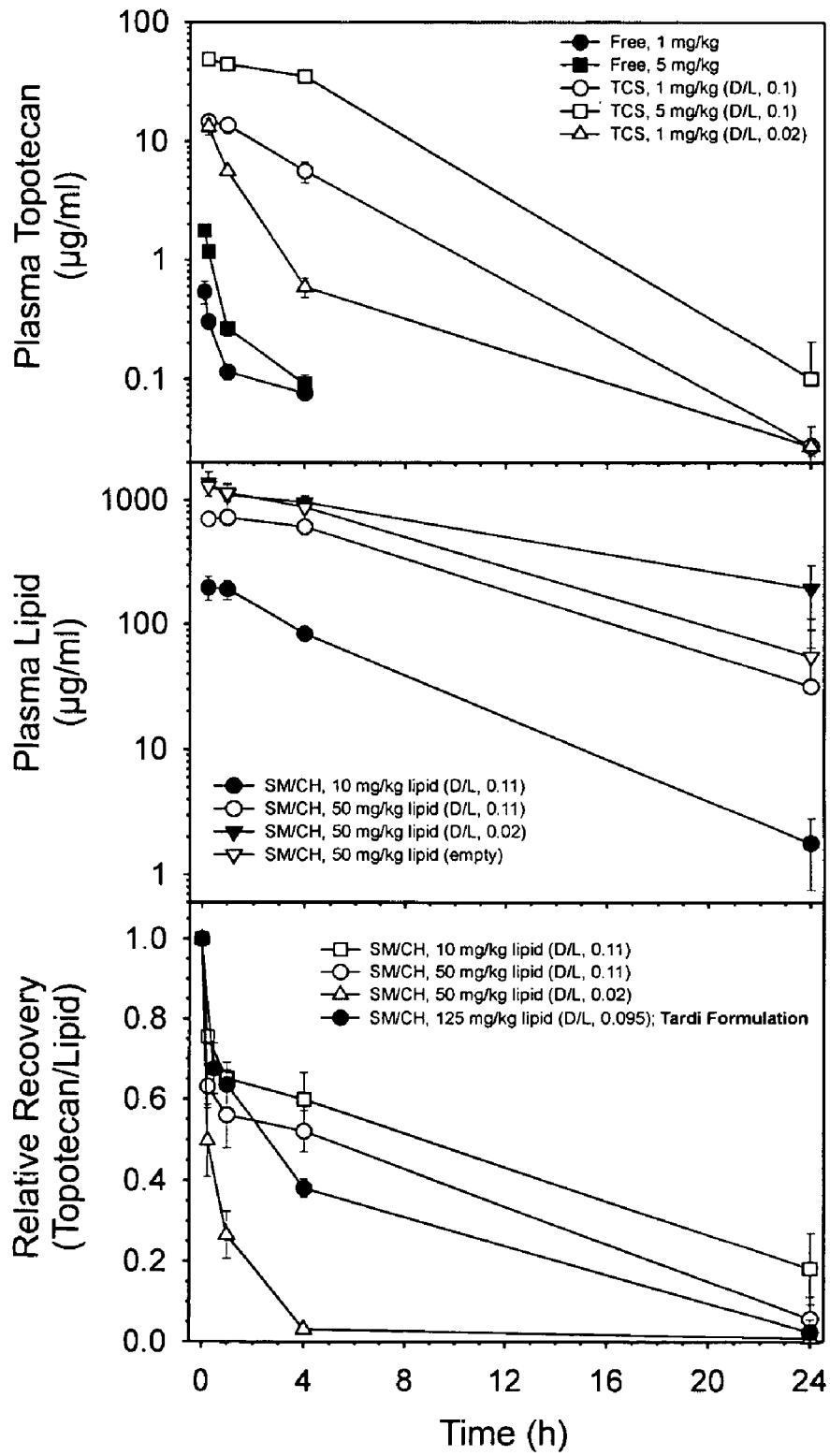
FIG. 1. Pharmacokinetics and drug leakage of topotecan encapsulated in SM/CH vesicles. Plasma Topotecan (μg/ml) (A); Plasma Lipid (μg/ml) (B); and Relative Recovery (Topotecan/Lipid) (C). Topotecan was encapsulated in 100 nm SM/CH (55/45 mol/mol) vesicles using the Mg-A23187 ionophore method as described in the Example section. Topotecan was assayed by a fluorescence assay (see, the Example section) and lipid was determined through the incorporation of a lipid marker, [$^3$H]-CHE. Data points represent the mean±SD of 4 mice. The SM/CH formulation prepared by the Mn-A23187 ionophore method is included in the bottom panel for comparison (from Tardi et al, *Cancer Res.*, 2000 submitted).

It has now been discovered that the anti-tumor activity of topotecan hydrochloride (Hycamtin™, SmithKline Beecham) encapsulated in sphingomyelin/cholesterol liposomes, such as sphingomyelin/cholesterol (55:45) liposomes, by a gradient loading method provides surprising clinical efficacy at lower doses, and with lower collateral toxicity, than free topotecan. The data demonstrates a dramatic increase in therapeutic index of liposome-encapsulated topotecan relative to the free drug. The present invention also provides a novel range of different dosages and dosage schedules, and a variety of drug:lipid ratio formulations of liposomal camptothecins, that are useful for treating solid tumors.

I. Compositions and Methods of Making Liposomal Camptothecins

Liposome, vesicle and liposome vesicle will be understood to indicate structures having lipid-containing membranes enclosing an aqueous interior. The structures can have one or more lipid membranes unless otherwise indicated, although generally the liposomes will have only one membrane. Such single-layered liposomes are referred to herein as "unilamellar." Multilayer liposomes are referred to herein as "multilamellar."

The liposomes that are used in the present invention are preferably formed from lipids which when combined form relatively stable vesicles. An enormous variety of lipids are known in the art which can be used to generate such liposomes. Preferred lipids include, but are not limited to, neutral and negatively charged phospholipids or sphingolipids and sterols, such as cholesterol. The selection of lipids is generally guided by consideration of, e.g., liposome size and stability of the liposomes in the bloodstream.

Preferred liposome compositions for use in the present invention include those comprising sphingomyelin and cholesterol. The ratio of sphingomyelin to cholesterol in the liposome composition can vary, but generally is in the range of from about 75/25 mol %/mol % sphingomyelin/cholesterol to about 30/50 mol %/mol % sphingomyelin/cholesterol, more preferably about 70/30 mol %/mol % sphingomyelin/cholesterol to about 40/45 mol %/mol % sphingomyelin/cholesterol, and even more preferably about 55/45 mol %/mol % sphingomyelin/cholesterol. Other lipids can be included in the liposome compositions of the present invention as may be necessary, such as to prevent lipid oxidation or to attach ligands onto the liposome surface. Generally, if lipids are included, the other inclusion of such lipids will result in a decrease in the sphingomyelin/cholesterol ratio. Liposomes of this type are known as sphingosomes and are more fully described in U.S. Pat. No. 5,814,335, the teachings of which are incorporated herein by reference.

A variety of methods are available for preparing liposomes as described in, e.g., Szoka, et al., *Ann. Rev. Biophys. Bioeng.* 9:467 (1980); U.S. Pat. Nos. 4,235,871; 4,501,728; 4,837,028, the text Liposomes, Marc J. Ostro, ed., Marcel Dekker, Inc., New York, 1983, Chapter 1; and Hope, et al., *Chem. Phys. Lip.* 40:89 (1986), all of which are incorporated herein by reference. The protocol for generating liposomes generally includes: mixing of lipid components in an organic solvent; drying and reconstituting liposomes in aqueous solvent; and sizing of liposomes (such as by extrusion), all of which are well known in the art.

Alternative methods of preparing liposomes are also available. For instance, a method involving detergent dialysis based self-assembly of lipid particles is disclosed and claimed in U.S. Pat. No. 5,976,567 issued to Wheeler, et al., which avoids the time-consuming and difficult to-scale drying and reconstitution steps. Further methods of preparing liposomes using continuous flow hydration are under development and can often provide the most effective large scale manufacturing process.

Preparation of liposomal camptothecins requires loading of the drug into the liposomes. Loading can be either passive or active. Passive loading generally requires addition of the drug to the buffer at the time of the reconstitution step. This allows the drug to be trapped within the liposome interior, where it will remain if it is not lipid soluble, and if the vesicle remains intact (such methods are employed, for example, in PCT Publication No. WO 95/08986, the teachings of which are incorporated herein by reference).

Active loading is in many ways preferable, and a wide variety of therapeutic agents can be loaded into liposomes with encapsulation efficiencies approaching 100% by using a transmembrane pH or ion gradient (see, Mayer, et al., *Biochim. Biophys. Acta* 1025:143–151 (1990) and Madden, et al., *Chem. Phys. Lipids* 53:37–46 (1990)). Numerous ways of active loading are known to those of skill in the art. All such methods involve the establishment of some form of gradient that draws lipophilic compounds into the interior of liposomes where they can reside for as long as the gradient is maintained. Very high quantities of the desired drug can be obtained in the interior, so much that the drug may precipitate out on the interior and generate a continuing uptake gradient.

Particularly preferred for use with the instant invention is ionophore mediated loading as disclosed and claimed in U.S. Pat. No. 5,837,282, the teachings of which are incorporated by reference herein. Basically, this method employs an ionophore in the liposome membrane to drive the generation of a pH gradient from a previously existing monovalent or divalent ion gradient.

An important characteristic of liposomal camptothecins for pharmaceutical purposes is the drug to lipid ratio of the final formulation. Drug:lipid ratios can be established in two ways: 1) using homogenous liposomes each containing the same drug:lipid ratio; or 2) by mixing empty liposomes with liposomes having a high drug:lipid ratio to provide a suitable average drug:lipid ratio. For different applications, different drug:lipid ratios may be desired. Techniques for generating specific drug:lipid ratios are well known in the art. Drug:lipid ratios can be measured on a weight to weight basis, a mole to mole basis or any other designated basis. Preferred drug:lipid ratios range from about 0.005 drug:lipid (by weight) to about 0.2 drug:lipid (by weight) and, more preferably, from about 0.01 drug:lipid (by weight) to about 0.02 drug:lipid (by weight).

A further important characteristic is the size of the liposome particles. For use in the present inventions, liposomes having a size of from about 0.05 microns to about 0.15 microns are preferred.

The present invention also provides liposomal camptothecin compositions in kit form. The kit can comprise a ready-made formulation, or a formulation which requires mixing of the medicament before administration. The kit will typically comprise a container that is compartmentalized for holding the various elements of the kit. The kit will contain the liposomal compositions of the present invention or the components thereof, possibly in dehydrated form, with instructions for their rehydration and administration The liposome compositions prepared, for example, by the methods described herein can be administered either alone or in a mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may also contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the composition may include lipid-protective agents which protect lipids against free-radical and lipid-peroxidative damages on storage. Lipophilic free-radical quenchers, such as $\alpha$.-tocopherol and water-soluble iron-specific chelators, such as ferrioxamine, are suitable.

Exemplary methods of making specific formulations of liposomal camptothecins and, in particular, liposomal topotecan are set out in the examples below.

II. Methods of Using Liposomal Camptothecins

Liposomal camptothecins are used, according to this invention, in the treatment of solid tumors in an animal, such as a human. The examples below set out key parameters of the drug:lipid ratios, dosages of camptothecin and lipid to be administered, and preferred dose scheduling to treat different tumor types.

Preferably, the pharmaceutical compositions are administered parenterally, i.e., intraarticularly, intravenously, intraperitoneally, subcutaneously or intramuscularly. More preferably, the pharmaceutical compositions are administered by intravenous drip or intraperitoneally by a bolus injection. The concentration of liposomes in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration can be increased to lower the fluid load associated with treatment. Alternatively, liposomes composed of irritating lipids can be diluted to low concentrations to lessen inflammation at the site of administration. The amount of liposomes administered will depend upon the particular camptothecin used, the disease state being treated and the judgement of the clinician, but will generally, in a human, be between about 0.01 and about 50 mg per kilogram of body weight, preferably between about 5 and about 40 mg/kg of body weight. Higher lipid doses are suitable for mice, for example, 50–120 mg/kg.

Dosage for the camptothecin will depend on the administrating physician's opinion based on age, weight, and condition of the patient, and the treatment schedule. A recommended dose for free topotecan in Small Cell Lung Cancer is 1.5 mg/M$^2$ per dose, every day for 5 days, repeated every three weeks. Because of the improvements in treatment now demonstrated in the examples, below, doses of topotecan in liposomal topotecan in humans will be effective at ranges as low as from 0.015 mg/M$^2$/dose and will still be tolerable at doses as high as 15 to 75 mg/M$^2$/dose, depending on dose scheduling. Doses may be single doses or they may be administered repeatedly every 4h, 6h, or 12h or every 1d, 2d, 3d, 4d, 5d, 6d, 7d, 8d, 9d, 10d or combination thereof. Preferred scheduling may employ a cycle of treatment that is repeated every week, 2 weeks, three weeks, four weeks, five weeks or six weeks or combination thereof. In one preferred embodiment, treatment is given once a week, with the dose typically being less than 1.5 mg/M$^2$. In another embodiment, the interval regime is at least once a week. In another embodiment, interval regime is at least once every two week, or alternatively, at least once every three weeks.

Particularly preferred topotecan dosages and scheduling are as follows:

| Dosage (mg/M$^2$/dose) | Period | Repeat Cycle every: |
|---|---|---|
| 0.15 | 1d × 5d | 3 weeks |
| 0.5 | 1d | 1 week |
| 1.5 | 1d | 1 week |
| 15 | 1d | 3 weeks |
| 50 | 1d | 3 weeks |

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

III. EXAMPLES

A. Materials and Methods

1. Materials. Topotecan (Hycamtin™, SmithKline Beecham) was purchased from the pharmacy at the British Columbia Cancer Agency. Sphingomyelin (SM) was purchased from Avanti Polar Lipids. Sphingomyelin from Northern Lipids was used in an early study, but was less soluble in ethanol than the Avanti version. Cholesterol (CH) and the divalent cation ionophore A23187 were purchased from Sigma. [$^3$H]-cholesterylhexadecylether (Dupont) was used as a lipid marker.

2. Mice. Female, ICR, BDF-1 or athymic nu/nu (6–8 weeks) were purchased from Harlan-Sprague Dawley (Indianapolis, Ind.). All animals were quarantined for one week prior to use. All studies were conducted in accordance with the guidelines established by the Canadian Council on Animal Care (CCAC) and the Institutional Animal Care and User Committee (IACUC).

3. Formulation of topotecan by the Mg-A23187 method. Topotecan was encapsulated in SM:CH (55:45, mol/mol) liposomes using the Mg-A23187 ionophore method according to U.S. Pat. No. 5,837,282. The initial drug-to-lipid ratio was 0.10 (w/w) and drug loading was typically 95–100%. The external buffer consisted of 10 mM PBS, pH 7.5 and 300 mM sucrose. All formulations were analyzed with respect to particle size, drug loading efficiency, pH, and drug and lipid concentration.

4. Drug preparation and dosing. Each vial of topotecan (Hycamtin™) was hydrated in 1.0 ml of sterile water, giving a topotecan concentration of 4.0 mg/ml. Subsequent dilutions were μl made in 0.9% sterile saline to maintain the low pH required for the lactone species of the drug. Unused drug in the water stock solution (4.0 mg/ml) was stored at 4° C. in the absence of light. Liposome encapsulated topotecan was diluted in 0.9% saline to the required concentration for administration. All drug administrations were at 10 ml/kg (200 μl/20 g mouse) via the lateral tail vein.

5. Pharmacokinetic and in vivo leakage studies. The pharmacokinetics and drug leakage of free and liposome encapsulated topotecan were evaluated in ICR mice over 24 h following i.v. administration via the lateral tail vein. Two different drug-to-lipid ratios, i.e., 0.10 (w/w) and 0.02 (w/w), were used to examine the influence of drug-to-lipid ratio and lipid dose on drug leakage and PK behavior. Encapsulated topotecan was administered at 1 mg/kg (10 or 50 mg/kg lipid) and 5 mg/kg topotecan (50 mg/kg lipid). Correspondingly, the PK behavior of free topotecan was evaluated at and 1 and 5 mg/kg. Total topotecan in blood was determined by a fluorescence assay preceded by precipitation of plasma proteins. Topotecan was quantified by spectrofluorimetry at an excitation (2.5 nm slit width) and emission wavelength (2.5 nm slit width) of 380 and 518 nm, respectively. Lipid levels in plasma were determined by liquid scintillation counting of the [$^3$H]-CHE label.

6. MTD studies. MTD studies were performed in the host mouse strain corresponding to each tumor model. Single dose and multidose MTD were determined by monitoring weight loss over time. The MTD was defined as the dose that resulted in 20% weight loss.

7. Myelosuppression and neutropenia studies. Alteration in peripheral blood cell levels as a consequence of topotecan administration was assessed over 4–6 weeks in ICR mice. Blood was collected into EDTA microtainer tubes at Day 1, 3, 5, 7, 14, and 21 following i.v. administration of free or liposome encapsulated topotecan at 10 mg/kg. Empty vesicles were administered as a control. CBC and differential analysis was performed at Central Labs for Veterinarians (Langley, BC) to quantify cellular levels, ratios and morphology.

8. Tumor Models. The L1210 murine leukemia model and the CT-26 murine colon metastases model were employed as in standard protocols. Human MX-1 and LX-1 cell lines were obtained from the DCTD Tumor Repository in Frederick, MD. These cell lines were received as tumor fragments and were propagated in NCr nude mice by serial transplantation of 3×3 mm fragments. Experiments were not initiated until the cell lines had been through 3 passages in nude mice and the tumor lines were restarted when the passage number reached 10.

9. Efficacy Studies. All dosing of free and liposomal topotecan was administered by the intravenous route at 10 ml/kg via the lateral tail vein. In the L1210 and CT-26 models, dosing occurred on day 1 (tumor cell injection=day 0). For the MX-1 and LX-1 tumor models, tumor volume was determined by repeated perpendicular measurements of tumor dimensions and using the formula:

Volume (mm$^3$)=($L \times W^2$)/2

Dosing was initiated in the MX-1 and LX-1 models when tumors had clearly demonstrated growth and were in the range 100–300 mm$^3$.

Since most drugs exhibit a balance between a biological effect and toxicity, it is useful to examine a parameter that incorporates both of these attributes. The most commonly employed parameter is therapeutic index (TI). Traditionally, therapeutic index is defined as:

$TI=LD_{50}/ED_{50}$

However, since it is no longer permissible to perform LD50 studies, therapeutic index for these studies has been defined as follows:

$TI=MTD/MED$.

In the above formula, MTD is the maximum tolerated dose, defined as that dose that causes a mean weight loss of 20% in a group of animals; and MED is the minimal effective dose, defined as the dose that produces an optimal % T/C value of ≦40 in the solid tumor models or an % ILS of 50±10% in the survival models.

B. Results

1. Pharmacokinetics and drug leakage. The influence of liposome encapsulation and drug-to-lipid ratio on plasma pharmacokinetics and drug leakage of topotecan was examined over 24 h in ICR mice. Liposome encapsulation of topotecan (drug-to-lipid ratio, 0.11, wt/wt) had a dramatic influence on the pharmacokinetics parameters of the drug (see, FIG. 1, top; and Table 1). At a 5 mg/kg dose of topotecan, a 164-fold increase in plasma AUC, a 24-fold increase in $C_{max}$ and a 24-fold increase in the plasma α half-life were observed for the liposomal drug relative to the free drug (see, Table 1). Historically, large improvements in AUC and plasma half-lives of liposomal drugs have resulted in enhanced delivery of the drug to disease-sites (such as tumors), a process known as "disease-site targeting".

The formulations used in this study were prepared by the Mg-A23187 ionophore method. There was an initial rapid release of drug in the first 10–30 minutes after iv administration (see, FIG. 1, bottom), followed by a more gradual release phase. The $t_{1/2release}$ for the Mn-A23187 and Mg-A23187 formulations were ~3 h and ~5–7 h, respectively; however, very little drug was present in either formulation at 24 h.

For most liposomal drug formulations, the pharmacokinetic properties of the encapsulated drug are controlled by the lipid composition and dose. Liposomal topotecan has been shown to exhibit exceptional anti-tumor activity, even at very low drug doses (0.5 mg/kg; drug-to-lipid ratio, 0.10, wt/wt). At these drug doses and drug-to-lipid ratio, liposome elimination from the plasma is expected to be rapid. Therefore, to determine whether the pharmacokinetics of topotecan at low doses could be improved, a low drug-to-lipid ratio (0.02, wt/wt) formulation of topotecan was investigated. Interestingly, in this study, the low drug-to-lipid ratio formulation released the drug much faster than the higher drug-to-lipid ratio (0.11, wt/wt) formulation. This result was unexpected.

TABLE 1

Pharmacokinetic parameters of free and liposomal topotecan.

| Formulation | Dose (mg/kg) | AUC (h · µg/ml) | Cmax (µg/ml) | Cl (ml/h) | $α_{1/2}$ (h) | $β_{1/2}$ (h) |
|---|---|---|---|---|---|---|
| Free | 1 | 1.97 | 0.75 | 13.9 | 0.14 | 11.8 |
|  | 5 | 2.77 | 2.17 | 49.6 | 0.26 | 11.4 |
| TCS | 1 | 65.7 | 16.3 | 0.417 | 2.79 |  |
|  | 5 | 453 | 51.0 | 0.302 | 6.16 |  |

All parameters were derived from one or two-compartment models using WINNONLIN PK modeling software.

Figure 2:
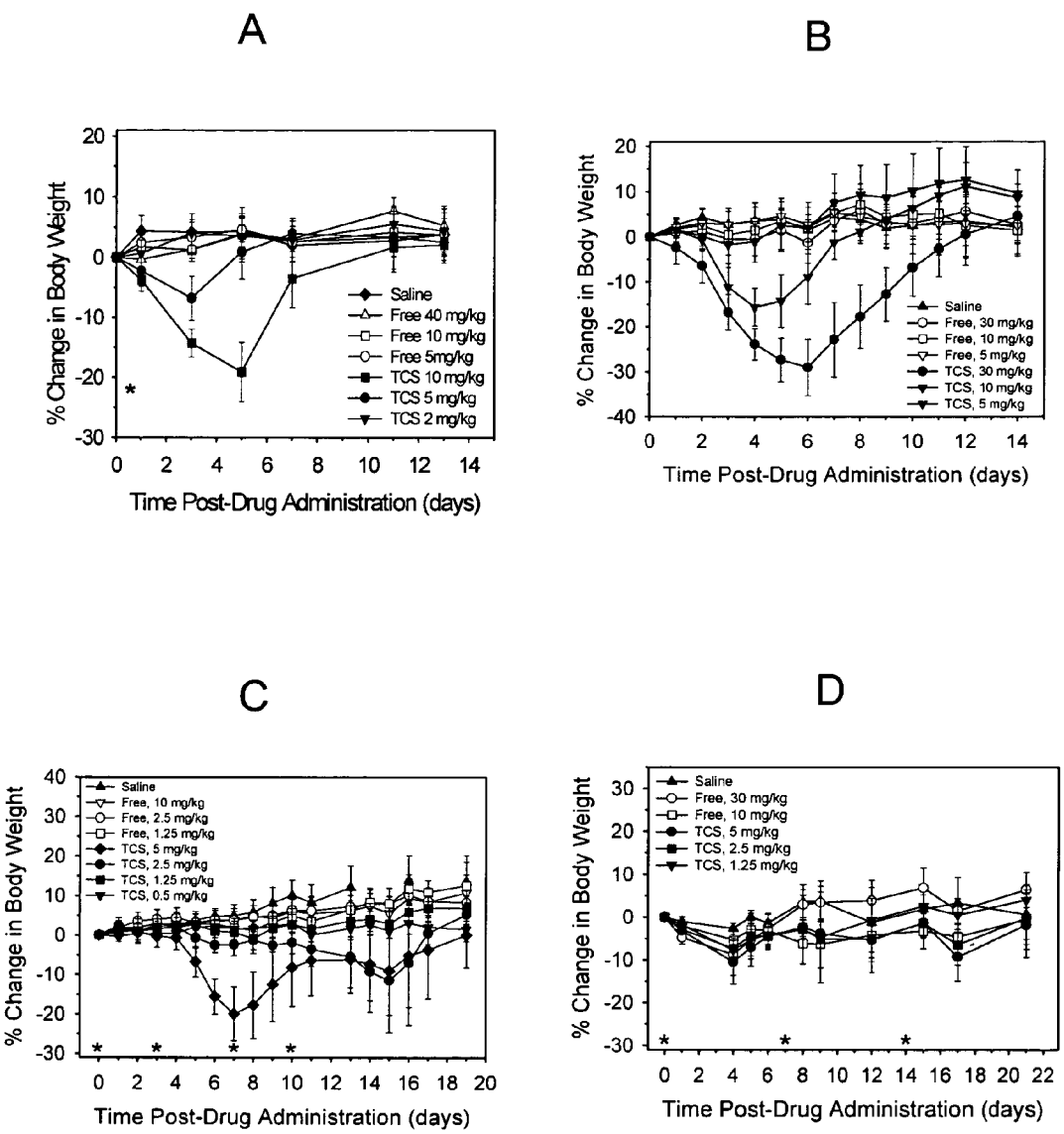
FIG. 2. Influence of mouse strain, dose schedule and liposome-encapsulation on topotecan tolerability in mice. Balb/c mice (CT-26); Single Dose (A); NCr nude mice (LX-1); Single Dose (B); NCr nude mice (MX-1); q3dx4 (C); and NCr nude mice (MX-1); q7dx3 (D). Body weights were monitored at least 3 times per week following drug administration. Data points represent the mean (±SD) % change in body weight for each treatment group (n=6–8 mice). Data is from studies NCTEF-002, NCTEF-003, NCTEF-006 and NCTEF-007.

2. Maximum tolerated doses. Single and multidose MTD studies were performed in tumor bearing Balb/c, BDF-1 and NCr nu/nu mice. Body weights of individual mice were monitored throughout each study to evaluate the general tolerability of free and liposomal topotecan and, where possible, to establish an MTD (see, FIG. 2). The maximum tolerated dose of liposomal topotecan was 10 mg/kg on a single administration, 7.5 mg/kg on a q7dx3 schedule and 5 mg/kg on a q3dx4 schedule. The reported $LD_{10}$ of free topotecan following a single intravenous infusion in mice is 75 mg/M² (~25 mg/kg) [Hycamtin™ product monograph]; however, very little weight loss was observed at doses up to 40 mg/kg, although this was considered the MTD due to acute responses. Drug quantities were limited so doses higher than 40 mg/kg (administered over 5–10 minutes) were not pursued. It has previously been indicated that the $LD_{10}$ of free topotecan on a qdx5 schedule is 14 mg/M2/dose (~4.7 mg/kg/dose) (Grochow, , et al., *Drug Metab. Dispos.* 20:706–713 (1992)).

3. Toxicity. The major dose-limiting toxicity of free topotecan administered daily in humans for 5 consecutive days (dx5) at 1.5 mg/M²/dose, the MTD, is non-cumulative myelosuppression. As mentioned earlier, humans are more sensitive than mice to myelosuppression and can only tolerate 11% of the MTD in mice (1.5 vs 14 mg/N²). In this regard, dogs have been shown to be a much better predictor of topotecan myelosuppression in humans (Burris, et al., *J. Natl. Cancer Inst.* 84:1816–1820 (1992)). However, mice should be suitable for comparing the relative myelosuppressive effects of free and liposome encapsulated topotecan.

topotecan (10 mg/kg). A significant reduction in circulating neutrophils was observed for liposomal topotecan relative to free topotecan (~10-fold), empty vesicles (~10-fold) or control animals (~20-fold). Total WBC levels and the lymphocyte sub-population were reduced approximately 2-fold for liposomal topotecan relative to control animals. No significant differences were observed in these parameters for free topotecan at the same dose. At day 21 post-injection total, WBC levels for liposomal topotecan remained approximately 2.5-fold lower than normal animals; however, neutrophils levels had recovered from a 20-fold decrease to a 3-fold decrease relative to normal mice. Lymphocyte levels remained ~2-fold lower than normal mice. No other significant differences were observed.

Analysis of serum chemistry parameters at day 3 post-injection revealed very few changes relative to untreated animals (see, Table 3). The only change of note was a statistically significant increase (~2-fold) in globulin levels and a concomitant decrease in the albumin/globulin ratio for animals treated with liposomal topotecan. No other significant changes were observed.

TABLE 2

Blood CBC and differential of ICR mice treated with a 10 mg/kg i.v. dose of free or liposome encapsulated topotecan.

| Treatment | Day Post-Injection | WBC ($\times 10^9$/L) | WBC Differential | | | | |
|---|---|---|---|---|---|---|---|
| | | | Neutro ($\times 10^9$/L) | Lympho ($\times 10^9$/L) | Mono ($\times 10^9$/L) | Eosino ($\times 10^9$/L) | Baso ($\times 10^9$/L) |
| Control | | 6.47 ± 1.62 | 0.937 ± 0.201 | 5.23 ± 1.45 | 0.180 ± 0.042 | 0.059 ± 0.039 | 0.056 ± 0.053 |
| Free | 3 | 6.70 ± 1.95 | 0.520 ± 0.200 | 5.90 ± 1.70 | 0.177 ± 0.072 | 0.031 ± 0.021 | 0.057 ± 0.040 |
| | 21 | 5.16 ± 1.18 | 0.480 ± 0.122 | 4.33 ± 0.93 | 0.247 ± 0.180 | 0.034 ± .016 | 0.088 ± 0.071 |
| TCS | 3 | 2.82 ± 1.05 | 0.048 ± 0.018 | 2.63 ± 0.87 | 0.109 ± 0.126 | 0.001 ± 0.001 | 0.034 ± 0.029 |
| | 21 | 2.54 ± 1.43 | 0.282 ± 0.167 | 2.06 ± 1.36 | 0.133 ± 0.142 | 0.019 ± 0.011 | 0.064 ± 0.060 |
| Empty | 3 | 4.68 ± 1.13 | 0.598 ± 0.238 | 3.66 ± 0.93 | 0.248 ± 0.168 | 0.081 ± 0.044 | 0.064 ± 0.055 |
| | 21 | 5.05 ± 0.64 | 0.898 ± 0.575 | 3.78 ± 0.88 | 0.263 ± 0.163 | 0.038 ± 0.036 | 0.072 ± 0.057 |

| Treatment | RBC ($\times 10^{12}$/L) | Hb (g/L) | Hc (L/L) | PLT ($\times 10^9$/L) |
|---|---|---|---|---|
| Control | 8.67 ± 0.93 | 142 ± 12 | 0.438 ± 0.045 | 717 ± 317 |
| Free | 8.47 ± 0.39 | 136 ± 05 | 0.444 ± 0.012 | 879 ± 145 |
| | 9.81 ± 0.37 | 154 ± 04 | 0.493 ± 0.014 | 907 ± 059 |
| TCS | 8.93 ± 0.76 | 141 ± 10 | 0.463 ± 0.033 | 564 ± 098 |
| | 9.41 ± 0.83 | 154 ± 12 | 0.486 ± 0.035 | 1009 ± 161 |
| Empty | 7.77 ± 0.30 | 130 ± 05 | 0.416 ± 0.014 | 863 ± 143 |
| | 9.36 ± 0.67 | 152 ± 08 | 0.483 ± 0.033 | 1366 ± 144 |

TABLE 3

Serum chemistry panel of ICR mice treated with a 10 mg/kg i.v. dose of free or liposome encapsulated topotecan-day 3 post-injection.

| Treamtent | BUN (nmol/L) | Creatinine (μmol/L) | TP (g/L) | Albumin (g/L) | Globulin (g/L) | Alb/Glob Ratio | Bilirubin (μmol/L) | Alk Phos (IU/L) | ALT (IU/L) | AST (IU/L) | CPK (IU/L) |
|---|---|---|---|---|---|---|---|---|---|---|---|
| Control | 11.3 ± 3.0 | 83 ± 6 | 46.7 ± 2.1 | 31.3 ± 1.5 | 15.3 ± 1.2 | 2.07 ± 0.15 | 4.7 ± 0.6 | 86 ± 12 | 27 ± 31 | 59 ± 22 | 87 ± 107 |
| Free | 9.4 ± 3.2 | 82 ± 18 | 48.0 ± 2.1 | 32.8 ± 1.3 | 15.2 ± 1.1 | 2.16 ± 0.15 | 3.8 ± 0.8 | 67 ± 35 | 13 ± 23 | 55 ± 10 | 56 ± 38 |
| TCS | 10.0 ± 3.9 | 96 ± 28 | 55.8 ± 11.8 | 28.8 ± 2.5 | 27.0 ± 10.1 | 1.18 ± 0.33 | 2.5 ± 0.6 | 73 ± 21 | 23 ± 17 | 77 ± 29 | 155 ± 54 |
| Empty | ND | 68 ± 13 | 49.3 ± 1.2 | 33.0 ± 1.7 | 16.3 ± 0.6 | 2.00 ± 0.17 | 4.3 ± 0.6 | 70 ± 10 | 17 ± 15 | 53 ± 6 | 56 ± 26 |

In a study, the maximal reduction in peripheral WBC counts occurred at day 3 post-injection following administration of liposomal topotecan. A comparison of peripheral blood cell levels and morphology was then made at day 3 following administration of free or liposome encapsulated topotecan or empty vesicles (see, Table 2). The dose used for this comparison was the MTD of liposome-encapsulated C. Efficacy Studies in Murine and Human Tumor Models: Single Dose Studies 1. L1210 Murine Leukemia. The intravenous L1210 murine leukemia model has been used extensively to evaluate differential activity between free and liposome encapsulated chemotherapeutic agents and was one of the original (1955–1975) models in the in vivo NCI screen of novel chemotherapeutic agents (Plowman, et al., Human tumor xenograft models in NCI drug development. In *"Anticancer Drug Development Guide: Preclinical Screening, Clinical Trials, and Approval"* (B. Teicher, Ed.), Humana Press Inc., Totowa (1997); Waud, Murine L1210 and P388 leukemias. In *"Anticancer Drug Development Guide: Preclinical Screening, Clinical Trials, and Approval"* (B. Teicher, Ed.), Humana Press Inc., Totowa (1997)). The model is rapid—the mean survival of untreated animals is typically ~7–8 days—and the administered tumor cells seed in the liver and bone marrow.

Administration of free topotecan as a single intravenous dose had minimal effect on survival in the L1210 model (see, FIG. 3A). At the highest dose of free topotecan, a median survival of 13 days (44% ILS) was observed. There was one long-term survivor (day 60) in this group. In contrast, a single i.v. administration of liposomal topotecan at either 5 or 10 mg/kg resulted in 100% survival at day 60 (see, FIG. 3B). Median survival for a 1 mg/kg dose was 13 days (44% ILS) and the survival curve was nearly identical to that of the free topotecan administered at 30 mg/kg—a 30-fold improvement in potency. At higher doses (30 mg/kg) of the liposomal topotecan, toxic deaths were observed. The MTD for liposomal topotecan was 20 mg/kg in BDF-1 mice after a single i.v. administration.

2. CT-26 Murine Colon Carcinoma. The murine CT-26 colon cell line is useful for drug screening since it readily grows as subcutaneous solid tumors or can be administered intravenously and used as a survival model. In addition, when the tumor cells are administered by intrasplenic injection, followed by splenectomy, the cells seed to the liver and give rise to an experimental metastases model that more closely resembles the clinical progression of colorectal cancer. The model has been used extensively and is described, for example, in detail elsewhere.

Figure 4:
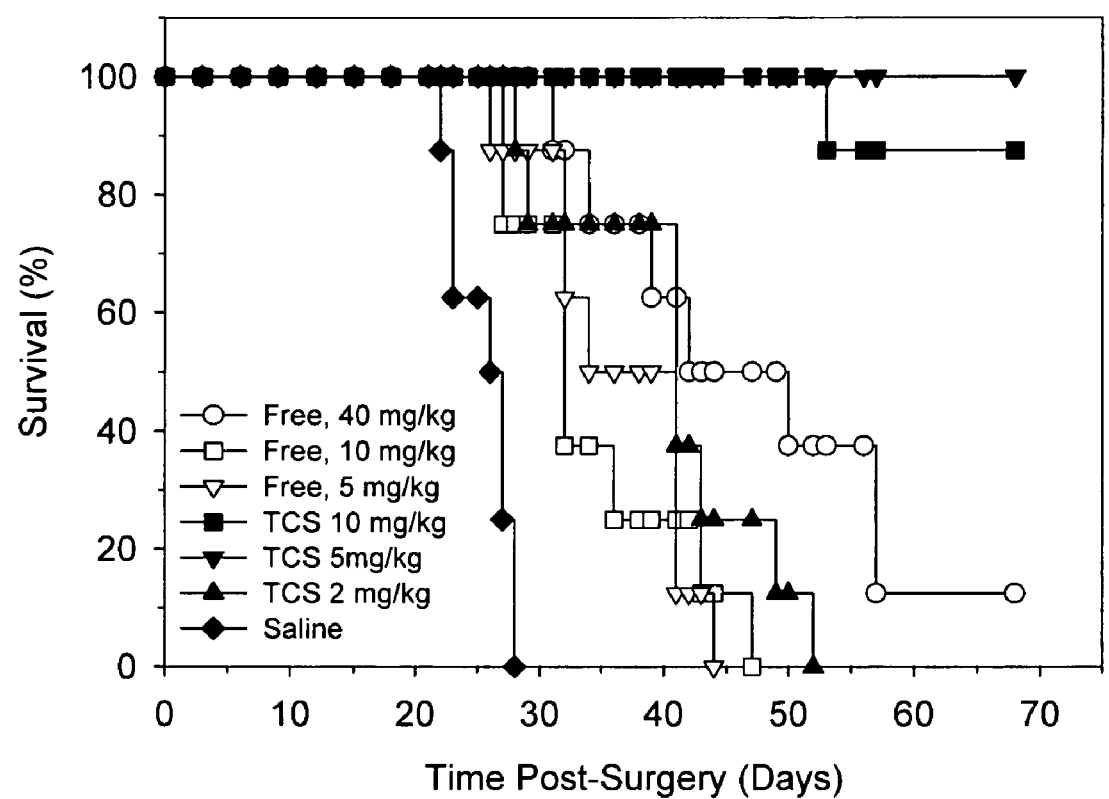
FIG. 4. Efficacy of free (A) and encapsulated (B) topotecan in an intrasplenic CT-26 murine colon metastases model-single dose. CT-26 cells (10$^4$ cells in 50 μl) were injected into the spleen of Balb/c mice on day 0. Topotecan was encapsulated in SM:CH (55:45) vesicles at a drug-to-lipid ratio of 0.10 (w/w) using the Mg-A23187 method as described in Experimental. All dilutions were made in sterile 0.9% saline immediately prior to injection. Drug administration was made via the lateral tail vein at 1 day post-tumor cell injection. Each group consisted of 8 animals. Data is from NCTEF-002.

In the CT-26 model, administration of a single dose of topotecan had a modest impact on survival resulting in % ILS of 23–60% over the dose range 5–40 mg/kg (see, FIG. 4). Liposome encapsulated topotecan, however, was highly active at doses greater than 5 mg/kg, resulting in 100% survival (8/8) at day 90. At 10 mg/kg, 87.5% survival (7/8) was observed at day 90; however, the tumor burden in dead animal was very low suggesting that this animal may have died due to other factors, such as infection related to myelosuppression. A dose response was observed for liposomal topotecan, with the 2 mg/kg dose giving an % ILS of 54%. This was determined to be the MED and was comparable to the % ILS (58%) achieved using free topotecan at 40 mg/kg —a 20-fold increase in potency.

3. MX-1 Human Breast Carcinoma. MX-1 is an experimental model of human breast cancer and has a reported doubling time of 3.9 days (NCI); in this study, the median doubling time was consistently 3.6–3.7 days. The tumor cell line was derived from the primary tumor of a 29-year-old female with no previous history of chemotherapy and is provided by the DCTD (NCI) tumor repository as a tumor fragment that is serially passaged in nude mice. Histologically, MX-1 is a poorly differentiated mammary carcinoma with no evidence of gland formation or mucin production. MX-1 was one of 3 xenograft models (MX-1, LX-1, CX-1) that comprised the NCI in vivo tumor panel and prescreen (1976–1986) for evaluating novel chemotherapeutic agents (Plowman, et al., Human tumor xenograft models in NCI drug development. In *"Anticancer Drug Development Guide: Preclinical Screening, Clinical Trials, and Approval"* (B. Teicher, Ed.), Humana Press Inc., Totowa (1997)). Since then, MX-1 has been incorporated into a larger panel of breast tumor models (12 in total) to reflect a shift in NCI strategy from "compound-oriented" discovery to "disease-oriented" discovery.

Figure 5:
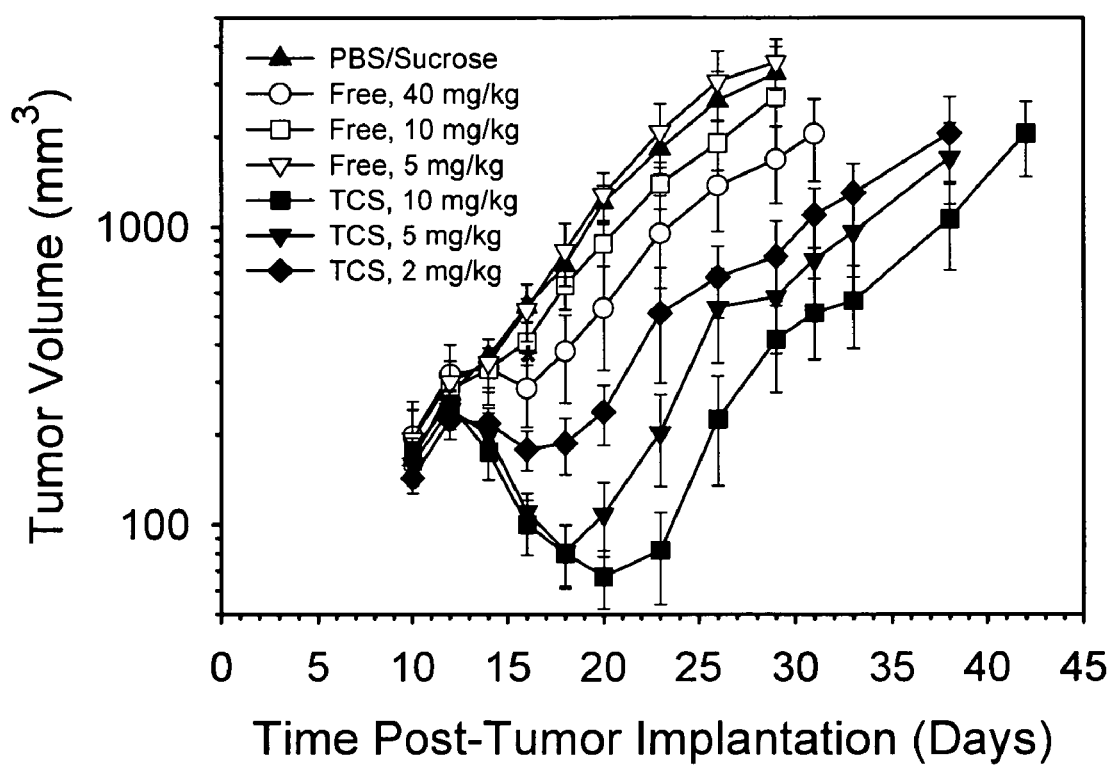
FIG. 5. Efficacy of free and encapsulated topotecan in subcutaneous MX-1 human breast xenografts-single dose. Topotecan was encapsulated in SM:CH (55:45) vesicles at a drug-to-lipid ratio of 0.10 (w/w) using the Mg-A23187 method as described in Experimental. All dilutions were made in sterile 0.9% saline immediately prior to injection. Drug administration was made via the lateral tail vein at 11 days post-tumor cell implantation when the tumors were 100–300 mm$^3$. Data points represent mean±SEM (n≦6). Data is from NCTEF-004.

In staged (100–300 mm$^3$) MX-1 tumors, free topotecan exhibited dose-dependent inhibition of tumor growth (see, FIG. 5; Table I). At the highest dose (40 mg/kg), an optimal % T/C of 24% was obtained; while optimal % T/C values for 10 and 5 mg/kg were 66% and 78%, respectively. No drug-related deaths were observed and all animals gained weight throughout the study. Liposome encapsulation of topotecan had a marked impact on % T/C, with optimal % T/C values of 8%, −49% and −62% following a single administration of the drug at 2, 5 or 10 mg/kg, respectively. A negative % T/C value is indicative of tumor volume regression from the original staged tumor size (100–300 mm$^3$). According to NCI guidelines, an optimal % T/C<10% is considered significant activity, while values<42% are the minimum acceptable limits for advancing a drug further in development (Corbett, T. et al., In vivo methods for screening and preclinical testing. In *"Anticancer Drug Development Guide: Preclinical Screening, Clinical Trials, and Approval"* (B. Teicher, Ed.), Humana Press Inc., Totowa (1997)). Liposome encapsulation increased the toxicity of topotecan, reducing the MTD to 10 mg/kg from>40 mg/kg for free topotecan.

4. LX-1 Human Lung Carcinoma. LX-1 is an experimental model of human small cell lung cancer (SCLC). The tumor cell line was derived from the surgical explant of a metastatic lesion found in a 48 year old male and is provided by the DCTD (NCI) tumor repository as a tumor fragment that is serially passaged in nude mice. The LX-1 model was part of the NCI in vivo tumor panel from 1976–1986 (Plowman, J. et al., Human tumor xenograft models in NCI drug development. In *"Anticancer Drug Development Guide: Preclinical Screening, Clinical Trials, and Approval"* (B. Teicher, Ed.), Humana Press Inc., Totowa (1997)) and, although used less frequently now, remains a useful xenograft model for comparative activity studies between free and liposomal drugs because of its rapid growth rate.

Figure 6:
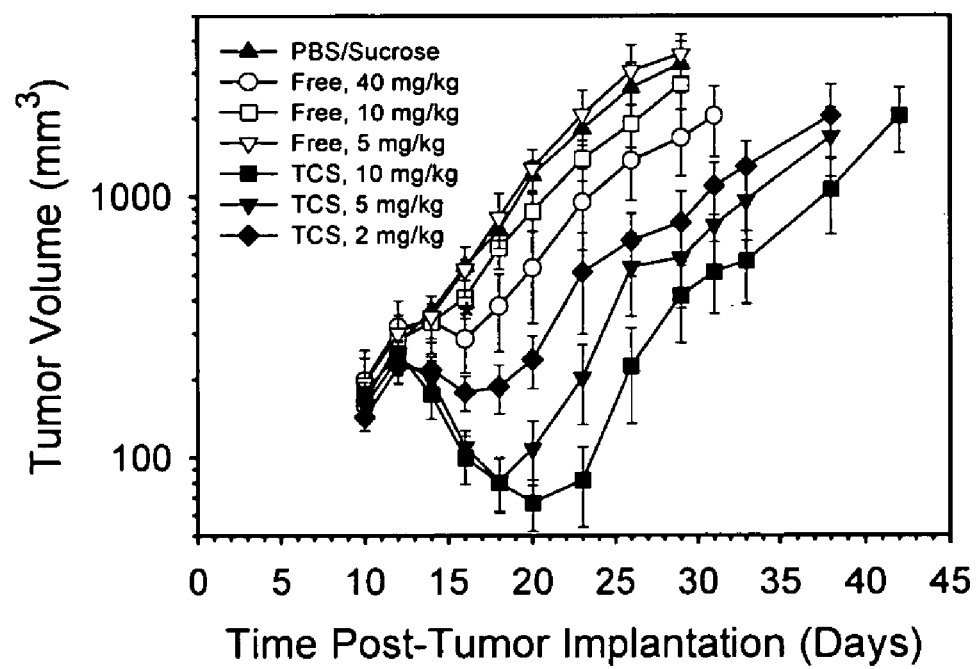
FIG. 6. Efficacy of free and encapsulated topotecan in subcutaneous LX-1 human SCLC xenografts-single dose. Topotecan was encapsulated in SM:CH (55:45) vesicles at a drug-to-lipid ratio of 0.10 (w/w) using the Mg-A23187 method as described in Experimental. All dilutions were made in sterile 0.9% saline immediately prior to injection. Drug administration was made via the lateral tail vein at 10 days post-tumor cell implantation when the tumors were 100–300 mm$^3$. Data points represent mean±SEM (n=6). Data is from NCTEF-003.

In general, the LX-1 model was less sensitive to the effects of topotecan than the MX-1 model, for both free and liposome-encapsulated drug (see, FIG. 6; Table I). Optimal % T/C values for free topotecan were 43%, 55% and 67% for doses of 30, 10 or 5 mg/kg, respectively. Anti-tumor activity was improved through encapsulation, resulting in % T/C values of 8%, 11% and 13% for doses of 30, 10, or 5 mg/kg, respectively. Interestingly, all of the liposomal topotecan doses exhibited similar activity. This was an early study and subsequent studies in other models (see, FIGS. 4–6) indicate dose response beginning at doses<5 mg/kg. This is consistent with the observation that camptothecin-class compounds (and presumably other antineoplastic agents) can exhibit "self-limiting" efficacy whereby, at doses above a critical threshold dose, no further activity benefits are observed (Thompson, *Biochim. Biophys. Acta* 1400: 301–319 (1998)). This situation could conceivably occur if the drug has limited tumor cell access or if the drug is acting on, and destroying, the tumor vasculature (i.e., has anti-angiogenic activity). In both instances, a higher dose of drug would be expected to have negligible benefit.

As observed in the L1210 study, encapsulation of topotecan enhanced the toxicity of the drug and reduced the MTD. The MTD in tumor-bearing nude mice was 10 mg/kg (~16% weight loss). At 30 mg/kg, 4/6 drug-related toxic deaths were observed and maximum weight loss reached ~29% (27–34% range).

D. Efficacy Studies in Murine and Human Tumor Models: Multiple Dose Studies

Figure 7:
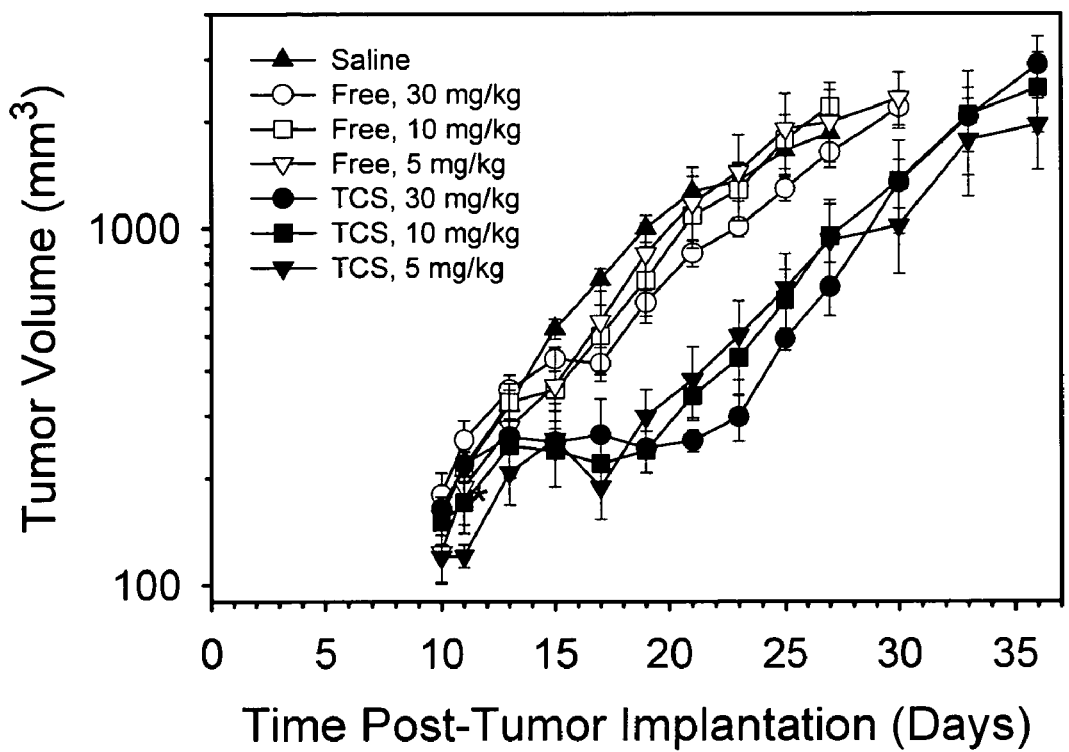
FIG. 7. Efficacy of free and encapsulated topotecan in subcutaneous MX-1 xenografts-q3dx4 schedule. Topotecan was encapsulated in SM:CH (55:45) vesicles at a drug-to-lipid ratio of 0.10 (w/w) using the Mg-A23187 method as described in Experimental. All dilutions were made in sterile 0.9% saline immediately prior to injection. Drug administration was made via the lateral tail vein beginning on day 10 (dosing days are indicated with an asterisk) post-tumor cell implantation. The dose (in mg/kg/dose) is indicated in parentheses in the figure. Data points represent mean±SEM (n=6). Data is from NCTEF-006.

1. MX-1 Human Breast Carcinoma. To address the effectiveness of multiple administration and prolonged exposure of the tumors to drug, two multiple dose protocols were examined in MX-1 xenografts—q3dx4 and q7dx3 schedules. On the q4dx3 schedule, free topotecan exhibited moderate activity at 2.5 and 10 mg/kg/dose and minimal activity at 1.25 mg/kg/dose (see, FIG. 7; Table II). Optimal % T/C values for free topotecan on this dosing schedule were 55%, 30% and 27% for 1.25, 2.5 and 10 mg/kg/dose, respectively. For the encapsulated topotecan administered on the same dosing schedule, optimal % T/C values were −15%, −100%, −100%, and −100% for 0.5, 1.25, 2.5 and 5 mg/kg/dose, respectively. All regressed tumors were monitored for 60 days. At the end of this period, all animals treated with ≧1.25 mg/kg/dose of liposomal topotecan were considered tumor free.

Figure 8:
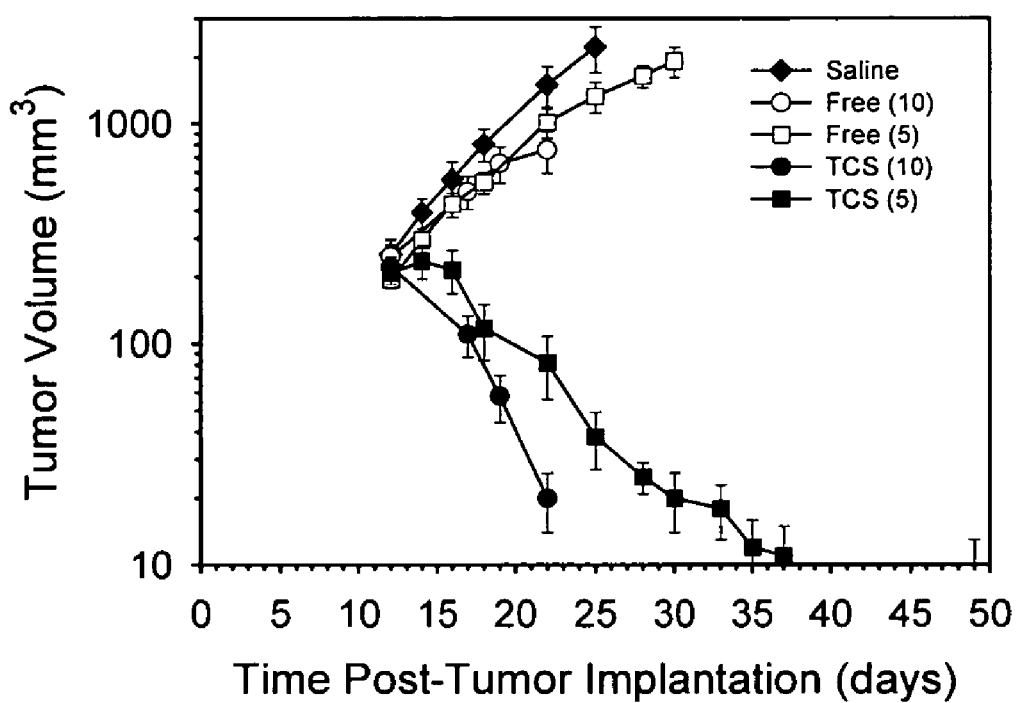
FIG. 8. Efficacy of free and encapsulated topotecan in subcutaneous MX-1 xenografts-q7dx3 schedule. Topotecan was encapsulated in SM:CH (55:45) vesicles at a drug-to-lipid ratio of 0.10 (w/w) using the Mg-A23187 method as described in Experimental. All dilutions were made in sterile 0.9% saline immediately prior to injection. Drug administration was made via the lateral tail vein on day 12, 17 and 24 post-tumor cell implantation. The dose (in mg/kg/dose) is indicated in parentheses in the figure. Data points represent mean±SEM (n=6). Data is from NCTEF-009.
Figure 9:
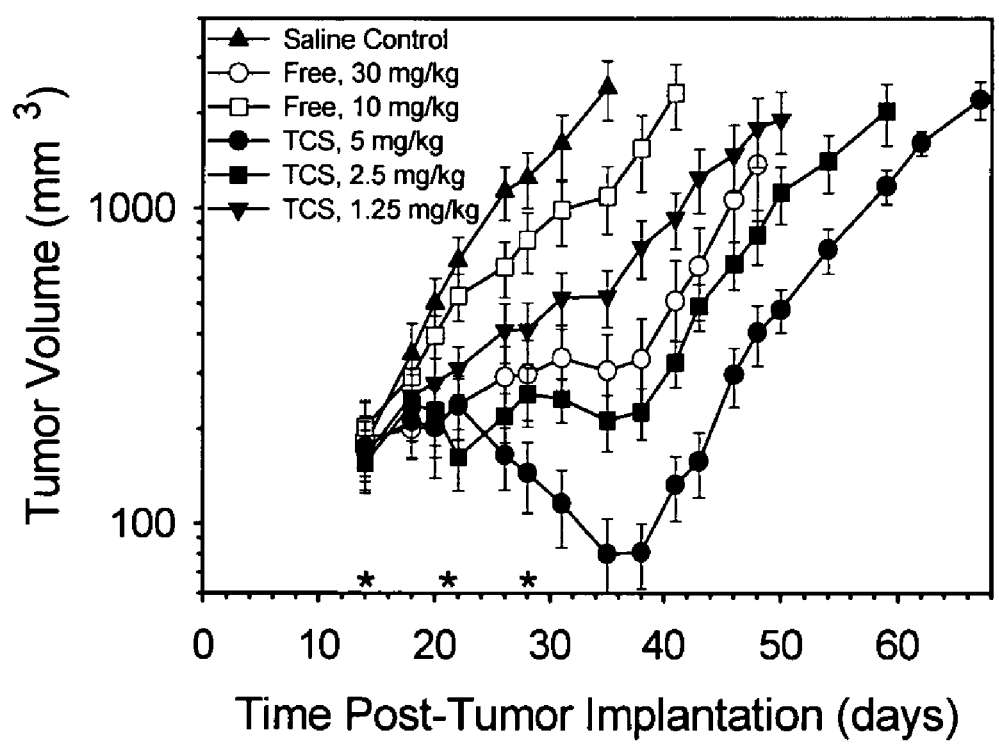
FIG. 9. Efficacy of free and encapsulated topotecan in subcutaneous LX-1 xenografts-q7dx3 schedule. Topotecan was encapsulated in SM:CH (55:45) vesicles at a drug-to-lipid ratio of 0.10 (w/w) using the Mg-A23187 method as described in Experimental. All dilutions were made in sterile 0.9% saline immediately prior to injection. Drug administration was made via the lateral tail vein on day 14, 21 and 28 post-tumor cell implantation. The dose (in mg/kg/dose) is indicated in the figure. Data points represent mean±SEM (n=6). Data is from NCTEF-007.

On a q7dx3 dosing schedule, little activity was observed with the free topotecan, either a 5 or 10 mg/kg/dose (see, FIG. 8; Table II). At the same doses, liposomal topotecan induced complete regression of the staged tumors. However, on this dosing schedule, 10 mg/kg/dose was too toxic and this portion of the study was halted as 6/6 toxic deaths (or euthanasia's) were observed by day 24.

2. LX-1 Human Lung Carcinoma. Initial studies (single dose) in the LX-1 model indicated that free topotecan was inactive at evaluated doses <30 mg/kg and liposomal topotecan inhibited tumor growth, but did not induce regression. To improve this activity, a multiple (q7dx3) schedule was examined for both free and liposomal topotecan. In this instance, considerably greater activity was observed for free topotecan compared to the single dose study and optimal % T/C values of 5 and 40 were obtained for 30 and 10 mg/kg/dose, respectively. Liposomal topotecan also exhibited significantly improved activity, resulting in complete regression (with subsequent re-growth) at 5 mg/kg/dose. Optimal % T/C values for liposomal topotecan in this model and dosing schedule were—55, 3 and 16 for 5, 2.5, 1.25 mg/kg/day, respectively.

3. Therapeutic Index (TI) Comparisons. The therapeutic index of free and liposomal topotecan was assessed in 4 different tumor models on several different dosing schedules (see, Table 4). The assumptions and definitions used to generate these numbers are found in Table III. In some instances, a true MED or MTD was not observed and was therefore estimated mathematically based on dose response trends. For instance, an acute MTD of 40 mg/kg was observed for free topotecan administered as a single bolus injection, but the true MTD (based on weight loss) would likely be closer to 60 mg/kg if the drug was infused over 5–10 minutes. Also, complicating the analysis somewhat was the level of potency of the liposomal formulation. Significant anti-tumor activity was achieved at low drug doses and the MED had to be estimated in certain studies. In these instances, a notation was made in Table 4.

In general, the increase in therapeutic index for liposomal topotecan was relatively large for single dose administration (5, 10, 15 and 18-fold, depending on the model) and decreased with increasing dosing frequency. This is illustrated in Table 4, where the $TI_{TCS}/TI_{Free}$ ratio was 4.7–7.5 and 3.3 for q7dx3 and q3dx4 schedules, respectively. The decrease in the $TI_{TCS}/TI_{Free}$ ratio with more frequent dosing is consistent with preclinical and clinical studies indicating that the efficacy and toxicity of free topotecan is schedule-dependent.

TABLE 4

Relative Therapeutic Indices of Free and Liposomal Topotecan in Murine and Human Tumor Models.[a]

| Tumor Model | Route of Inoculation | Dosing Schedule | $TI_{Free}$ | $TI_{TCS}$ | $TI_{TCS}/TI_{Free}$ |
|---|---|---|---|---|---|
| L1210 (murine leukemia) | i.v. | single | 1.3 (2.0)[b] | 20 | 15.4 (10)[b] |
| CT-26 (murine colon) | i.s. | single | 1.0 (1.5)[b] | 5.0 | 5 (3.3)[b] |
| MX-1 (human breast) | s.c. | single | 1.4 (2.1)[b] | 25 | 17.9 (11.9)[b] |
|  |  | q3dx4 | 15 | 50[c] | 3.3 |
|  |  | q7dx3 | 2.0 | 15.0[c] | 7.5 |
| LX-1 (human lung) | s.c. | single | 1.3 (2.0)[b] | 13.3 | 10.2 (6.7)[b] |
|  |  | q7dx3 | 4.0 | 18.8 | 4.7 |

[a]based on data in Table II and III; formulas and definitions in Table IV.
[b]obtained using an acute MTD of 40 mg/kg; second value is based on an estimated MTD (body weight)
[c]a conservative estimate that may be ~2-fold greater; difficult to assess the MED due to high activity at low doses.

E. Discussion

Topotecan is an excellent candidate for liposome encapsulation. Briefly, topotecan is cell-cycle specific (S-phase) and activity is greatly enhanced with prolonged exposure, topotecan exhibits rapid plasma pharmacokinetics and the drug needs to be maintained below pH 6.0 to retain biological activity. This is an ideal scenario for using a relatively non-leaky liposome formulation (such as SM:CH, 55:45) that has an acidic aqueous core. The required acidic interior can be produced, for example, by pH-loading or ionophore loading methodology. Here, it has been demonstrated that encapsulation of topotecan in SM/CH liposomes by the Mg-A23187 method results in dramatic enhancements in anti-tumor efficacy. Modest enhancement of toxicity was also observed for liposomal topotecan, but this was largely offset by substantial dose reductions that achieved comparable and, in most instances, superior efficacy relative to the free drug.

Therapeutic index (TI) is a useful parameter of drug activity, as it is measure of the ratio of toxicity (MTD) to biological activity (user defined endpoint, i.e., MED, $ED_{50}$, or $ED_{80}$). In general, the lower the TI, the greater the risk of toxicity since the dose of drug required to elicit a biological effect approaches the MTD. Therapeutic index is particularly useful for the evaluation of liposomal drugs since the relative change in TI can be used to define the benefit (or lack thereof) of encapsulation. As demonstrated herein, the TI improved from 3–18 fold depending on the model and dose schedule used. Therefore, the improvement in biological activity observed following liposome encapsulation of topotecan more than compensates for any increases in toxicity.

Without intending to be bound by any theory, it is thought that the significant improvements in anti-tumor activity and the increased toxicity of the liposomal form of the drug result from improved pharmacokinetics and the maintenance of the drug in the active lactone form. In these studies, 84% of topotecan was present in plasma as the lactone species after 24 h compared to 48% lactone for free topotecan after only 5 minutes. Moreover, when the same dose (10 mg/kg) of free and liposomal topotecan was administered intravenously in mice, the concentration of lactone was ~40-fold higher at times<1 h. At 24 h, the lactone plasma concentration for liposomal drug was 5.4 μg/ml compared to 1.5 μg/ml at 5 minutes for free drug—still 3.5-fold greater than the peak lactone concentration for free topotecan.

TABLE I

Summary of Single Dose Anti-Tumor Activity and Toxicity Parameters

| Model | | Dose | % T/C[a] | T-C[b] | % ILS[c] | LCK[d] | TF[e] | DRD[f] | MWL[g] |
|---|---|---|---|---|---|---|---|---|---|
| L1210 | Free | 5 | | | 11 | | 0/8 | 0/8 | + |
| (i.v.) | Free | 10 | | | 22 | | 0/8 | 0/8 | + |
| NCTEF-005 | Free | 20 | | | 33 | | 0/8 | 0/8 | + |
| | Free | 30 | | | 44 | | 0/8 | 0/8 | + |
| | Free | 40 | | | 55 | | 0/8 | 0/8 | + |
| | TCS | 1 | | | 44 | | 0/8 | 0/8 | + |
| | TCS | 5 | | | ** | | 8/8 | 0/8 | + |
| | TCS | 10 | | | ** | | 8/8 | 0/8 | −9.7 |
| | TCS | 20 | | | ** | | 7/7 | 1/8 | −14.8 |
| | TCS | 30 | | | ** | | 3/3 | 5/8 | −23.4 |
| CT-26 | Free | 5 | | | 31 | | 0/8 | 0/8 | + |
| (i.s.) | Free | 10 | | | 23 | | 0/8 | 0/8 | + |
| NCTEF-005 | Free | 40 | | | 58 | | 1/8 | 0/8 | −0.4 |
| | TCS | 2 | | | 54 | | 0/8 | 0/8 | + |
| | TCS | 5 | | | ** | | 8/8 | 0/8 | −6.8 |
| | TCS | 10 | | | ** | | 7/8 | 0/8 | −19.1 |
| MX-1 | Free | 5 | 78 | 0.2 | 0 | 0.02 | 0/6 | 0/6 | + |
| (s.c.) | Free | 10 | 66 | 1.4 | 13 | 0.12 | 0/6 | 0/6 | + |
| NCTEF-004 | Free | 40 | 24 | 4.2 | 35 | 0.35 | 0/6 | 0/6 | + |
| | TCS | 2 | 8 | 7.4 | 65 | 0.62 | 0/6 | 0/6 | + |
| | TCS | 5 | −49 | 10.2 | 74 | 0.85 | 0/6 | 0/6 | −0.4 |
| | TCS | 10 | −62 | 14.2 | 83 | 1.19 | 1/6 | 0/6 | −18.3 |
| LX-1 | Free | 5 | 67 | 1.4 | 0 | 0.13 | 0/6 | 0/6 | + |
| (s.c.) | Free | 10 | 55 | 1.9 | 0 | 0.18 | 0/6 | 0/6 | + |
| NCTEF-003 | Free | 30 | 43 | 2.9 | 7 | 0.27 | 0/6 | 0/6 | −1.3 |
| | TCS | 5 | 13 | 7.9 | 30 | 0.74 | 0/6 | 0/6 | −1.7 |
| | TCS | 10 | 11 | 8.7 | 22 | 0.82 | 0/6 | 0/6 | −15.6 |
| | TCS | 30 | 8 | 9.9 | 22 | 0.93 | 0/6 | 4/6 | −29.0 |

[a]optimal % T/C following final treatment. Negative value indicates tumor regression.
[b]tumor growth delay (difference in time for treated and control tumors to reach 500 mm³).
[c]increase in lifespan relative to untreated animals (expressed as %).
[d]log cell kill (gross).
[e]tumor free animals at the end of study (i.e. no visible tumors or long term survivors).
[f]drug related deaths.
[g]maximum mean weight loss per treatment group.
[h]positive weight change (i e at no time did weight decrease below pre-treatment weight).
**long term survivors

TABLE II

Summary of Multiple Dose Anti-Tumor Activity and Toxicity Parameters

| Model | | Dose | % T/C[a] | T-C[b] | % ILS[c] | LCK[d] | TF[e] | DRD[f] | MWL[g] |
|---|---|---|---|---|---|---|---|---|---|
| MX-1 | Free | 1.25 | 55 | 2.0 | 20 | 0.17 | 0/6 | 0/6 | +[h] |
| (q3dx4) | Free | 2.5 | 30 | 5.0 | 55 | 0.42 | 0/6 | 0/6 | + |
| NCTEF-006 | Free | 10 | 27 | 2.5 | 52 | 0.21 | 1/6 | 0/6 | + |
| | TCS | 0.5 | −15 | 23.5 | 157 | 1.96 | 1.6 | 0/6 | −0.3 |
| | TCS | 1.25 | −100 | ** | ** | | | 6/6 | 0/6 | −1.0 |
| | TCS | 2.5 | −100 | ** | ** | | | 6/6 | 0/6 | −11.5 |
| | TCS | 5 | −100 | ** | ** | | | 6/6 | 0/6 | −20.0 |
| MX-1 | Free | 5 | 58 | 1.8 | 27 | 0.15 | 0/6 | 0/6 | + |
| (q7dx3) | Free | 10 | 61 | 2.0 | ND[1] | | 0/6 | 0/6 | −0.8 |
| NCTEF-009 | TCS | 5 | −100 | ** | ** | | | 6/6 | 0/6 | −7.6 |
| | TCS | 10 | −100 | ND[1] | ND[1] | | | 6/6 | 6/6 | −29.0 |

TABLE II-continued

Summary of Multiple Dose Anti-Tumor Activity and Toxicity Parameters

| Model | | Dose | % T/C[a] | T-C[b] | % ILS[c] | LCK[d] | TF[e] | DRD[f] | MWL[g] |
|---|---|---|---|---|---|---|---|---|---|
| LX-1 | Free | 10 | 40 | 2.0 | 21 | 0.14 | 0/6 | 0/6 | −6.2 |
| (q7dx3) | Free | 30 | 5 | 20.9 | 58 | 1.53 | 0/6 | 0/6 | −8.8 |
| NCTEF-007 | TCS | 1.25 | 16 | 10.8 | 54 | 0.79 | 0/6 | 0/6 | −7.7 |
| | TCS | 2.5 | 3 | 23.2 | 79 | 1.70 | 0/6 | 0/6 | −7.3 |
| | TCS | 5 | −55 | 30.2 | 100 | 2.22 | 0/6 | 0/6 | −10.5 |
| LX-1 | Free | 10 | 28 | 4.4 | 41 | | 0/6 | 0/6 | −3.6 |
| (q7dx3) | Free | 30 | 9 | 25 | 72 | | 0/6 | 2/6 | −16.4 |
| NCTEF-011 | TCS | 7.5 | ND[i] | ND[i] | ND[i] | | 0/6 | 6/6 | >−30 |
| | TCS | 0.75 | 27 | 11.2 | 50 | | 0/6 | 0/6 | −1.3 |

[a]optimal % T/C following final treatment. Negative value indicates tumor regression.
[b]tumor growth delay (difference in time for treated and control tumors to reach 500 mm3).
[c]increase in lifespan relative to untreated animals (expressed as %).
[d]log cell kill (gross).
[e]tumor free animals at the end of study (i.e. no visible tumors or long term survivors).
[f]drug related deaths.
[g]maximum mean weight loss per treatment group.
[h]positive weight change (i.e. at no time did weight decrease below pre-treatment weight).
[i]not determined; toxic deaths in the liposome-encapsulated group.
***"cures"; no visible tumors by day 60.

TABLE III

Definitions and Formulas for Toxicity and Anti-Tumor Activity Parameters

| | |
|---|---|
| DRD | Drug-related death. A death was considered drug-related if the animal died or was euthanized within 15 days following the final treatment with drug AND its tumor weight was less than the lethal burden on control mice, or its weight loss was greater than 20% that of the control animals. |
| $GI_{50}$ | The concentration of drug that causes 50% growth inhibition in a population of cells in vitro. The NCI renamed the $IC_{50}$ parameter to emphasize the correction for cell count at time zero. Therefore, the formula is: $GI_{50} = (T - T_o)/(C - T_o) \times 100 = 50$ T and $T_o$ are the optical densities at 48 and 0 h, respectively; C is the control (cell count) optical density at 0 h. |
| % ILS | Increase in lifespan (in percent). For survival models this is calculated using the median survival times for the treated ($T_{treat}$) and control ($T_{cont}$) animals, according to: $(T_{treat} - T_{cont})/T_{cont} \times 100$ For the solid tumor models, the time for tumors to reach 2000 mm³ (~10% of body weight) was used as an ethical cutoff instead of median survival. |
| LCK | Log cell kill (gross). This parameter estimates the number of $log_{10}$ units of cells killed at the end of treatment, according to the formula: $(T - C) \times 0.301/$median doubling time Net log cell kill can be calculated by subtracting the duration of treatment from the tumor growth delay (T − C) parameter as follows: $[(T - C) - $duration of treatment$] \times 0.301/$median doubling time A log cell kill of 0 indicates that the cell population at the end of treatment is the same as it was at the onset of treatment. However, a log cell kill of 4, for example, indicates a 99.99% reduction in the initial cell population. |
| MBWL | Maximum body weight loss (in percent). The animals are weighed prior to the first administration of the drug (Wi) and on various days during the study (Wd). The percent change in body weight is calculated by: $MBWL = (W_d - W_i)/W_i \times 100$ |
| MED | Minimum effective dose. This is a somewhat arbitrary parameter. For these studies we have defined the MED as the lowest dose achieving an optimal % T/C ≤ 40 (for solid tumor models) or a % ILS of 40–60% (for survival models). |
| MTD | Maximum tolerated dose. Dose of drug that results in a MBWL of ≦20%. |
| % T/C | Optimal ratio of treated vs control tumors obtained following the first course of treatment. These values are obtained by subtracting the median tumor weight on the first day of treatments ($T_i$ or $C_i$) from the tumor weights on each observation day according to the following formula: % T/C = $(\Delta T/\Delta C) \times 100$, where $\Delta T > 0$, or % T/C = $(\Delta T/T_i) \times 100$, where $\Delta T < 0$ According to NCI activity criteria, the following scoring system applies (Plowman, et al., Human tumor xenograft models in NCI drug development. In "Anticancer Drug Development Guide: Preclinical Screening, Clinical Trials, and Approval" (B. Teicher, Ed.), Humana Press Inc., Totowa (1997)[22]: 0 = inactive, % T/C > 40 1 = tumor inhibition, % T/C range 1–40 2 = tumor stasis, % T/C range 0 to −40 3 = tumor regression, % T/C range −50 to −100 4 = % T/C range −50 to −100 and >30% tumor-free mice |
| TGD | Tumor growth delay (also represented as T − C). This parameter expresses the difference in time (in days) for treated and control tumors to attain an arbitrary size (typically 500 or 1000 mm³). |
| TI | Therapeutic index. Therapeutic index is the ratio of a toxicity parameter (i.e. $LD_{50}$, $LD_{10}$, MTD) and a biological activity parameter (i.e. $ED_{50}$ – the dose that causes a defined biological response in 50% of the treatment group). In general, TI describes the margin of safety for a drug. For animal model studies this is traditionally described by the formula: TI = $LD_{50}/ED_{50}$ However, since it is no longer ethically permissible to perform $LD_{50}$ studies, we have defined therapeutic index for these studies as: TI = MTD/MED |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A liposomal topotecan unit dosage form, said unit dosage form comprising:
   a lipid; and
   a topotecan dosage of 0.01 mg/M$^2$/dose to 7.5 mg/M$^2$/dose, wherein said liposomal topotecan unit dosage form has a drug:lipid ratio by weight of 0.05 to 0.2 and wherein said lipid comprises a mixture of sphingomyelin and cholesterol.

2. A method of treating solid tumors in a mammal, said method comprising:
   administering to said mammal having a solid tumor of the lung, mammary and/or colon a liposomal topotecan formulation comprising 0.01 mg/M$^2$/dose to 7.5 mg/M$^2$/dose of topotecan for an interval regime, wherein said liposomal topotecan formulation has a drug:lipid ratio by weight of 0.05 to 0.2 and wherein said liposome comprises a mixture of sphingomyelin and cholesterol for a time and under conditions effective to reduce and/or delay growth of the solid tumor mass.

3. The method of treating solid tumors of claim 2, wherein said interval regime is at least once a week.

4. The method of treating solid tumors of claim 2, wherein said interval regime is at least once every two weeks.

5. The method of treating solid tumors of claim 2, wherein said interval regime is at least once every three weeks.

6. The method of treating solid tumors of claim 2, wherein said interval regime is once a day for at least two consecutive days.

7. A liposomal camptothecin unit dosage form, said unit dosage form comprising a lipid, a camptothecin dosage of from 0.015 mg/M$^2$/dose to 1 mg/M$^2$/dose and having a drug:lipid ratio by weight of 0.05 to 0.2 and wherein said lipid comprises a mixture of sphingomyelin and cholesterol.

8. The liposomal topotecan unit dosage form of claim 1, wherein said drug:lipid ratio by weight is 0.05 to 0.15.

9. The liposomal topotecan unit dosage form of claim 1, wherein said lipid comprises sphingomyelin and cholesterol in a molar ratio of 70:30 to 40:45.

10. The liposomal topotecan unit dosage form of claim 1, comprising from 1 mg/M$^2$/dose to 4 mg/M$^2$/dose of topotecan.

* * * * *

UNITED STATES PATENT AND TRADEMARK OFFICE
CERTIFICATE OF CORRECTION

PATENT NO. : 7,060,828 B2  
APPLICATION NO. : 09/896811  
DATED : June 13, 2006  
INVENTOR(S) : Thomas D. Madden et al.

Page 1 of 1

It is certified that error appears in the above-identified patent and that said Letters Patent is hereby corrected as shown below:

Title Page
Item (56) Other Publications, "Apostolidou, E., G. Garcia-Manero, et al. "Phase I Study of OSI-211, a Novel Liposomal Topoisomerase 1 (Topo 1) Inhibitor, in Patients withs Refractory Leukemia," *Blood*, 2002. Abstract #4575." should read as: --Apostolidou, E., G. Garcia-Manero, et al. "Phase I Study of OSI-211, a Novel Liposomal Topoisomerase 1 (Topo 1) Inhibitor, in Patients with Refractory Leukemia," *Blood*, 2002. Abstract #4575.--

Page 4
Item (56) Other Publications, "Desjardins, J. P., D. L. Emerson, et al. "Biodistribution of NX 211, liposomal GI147211, in tumor bearing mice." *Proc Amer Assoc Cancer Res 41*702, Mar. 2000. Abstract #4467." Should read as --Desjardins, J. P., D. L. Emerson, et al. "Biodistribution of NX 211, liposomal GI147211, in tumor bearing mice." *Proc Amer Assoc Cancer Res 41*:702, Mar. 2000. Abstract #4467.--

Signed and Sealed this

Third Day of April, 2007

JON W. DUDAS  
*Director of the United States Patent and Trademark Office*